(12) United States Patent
Wu et al.

(10) Patent No.: US 7,411,060 B2
(45) Date of Patent: Aug. 12, 2008

(54) TRANSGENIC FISH GERMLINE EXPRESSION DRIVEN BY LIVER FATTY ACID BINDING (L-FABP) GENE PROMOTER AND APPLICATIONS THEREOF

(75) Inventors: Jen-Leih Wu, Taipei (TW); Guor Mour Her, Taipei (TW)

(73) Assignee: Academia Sinica, Taipei (TW)

( * ) Notice: Subject to any disclaimer, the term of this patent is extended or adjusted under 35 U.S.C. 154(b) by 297 days.

(21) Appl. No.: 10/717,573

(22) Filed: Nov. 21, 2003

(65) Prior Publication Data

US 2004/0209833 A1 Oct. 21, 2004

Related U.S. Application Data

(60) Provisional application No. 60/473,210, filed on May 27, 2003, provisional application No. 60/463,035, filed on Apr. 16, 2003.

(51) Int. Cl.
*C07H 21/04* (2006.01)
*A01K 67/033* (2006.01)

(52) U.S. Cl. .................................... 536/24.1
(58) Field of Classification Search ........................ None
See application file for complete search history.

(56) References Cited

U.S. PATENT DOCUMENTS

| | | | | |
|---|---|---|---|---|
| 5,625,124 | A * | 4/1997 | Falk et al. | 800/3 |
| 6,503,498 | B1 * | 1/2003 | Gerard et al. | 424/93.2 |
| 6,719,969 | B1 * | 4/2004 | Hogaboam et al. | 424/85.2 |
| 6,794,154 | B1 * | 9/2004 | Yamanouchi et al. | 435/7.8 |

OTHER PUBLICATIONS

NCBI Report for GenBank Accession No. AL929535, Feb. 7, 2003, pp. 1-47.*
NCBI Report for GenBank Accession No. AC139623, Feb. 7, 2003, pp. 1-60.*
NCBI Report for GenBank Accession No. BX240588, Jan. 27, 2003, p. 1.*
Zhong TP, Kaphingst K, Akella U, Haldi M, Lander ES, Fishman MC. Zebrafish genomic library in yeast artificial chromosomes. Genomics. Feb. 15, 1998, vol. 48, No. 1:136-8.*
Dooley, Kimberly et al., Zebrafish: a model system for the study of human disease; Genetics of disease; p. 252-256.
Simon, Theodore C., et al., Use of Transgenic Mice to Map cis-Acting Elements in the Liver Fatty Acid-binding Protein Gene (Fabpl) That Regulates Its Cell Lineage-specific, Differentiation-dependent, and Spatial Patterns of Expression in the Gut Epithelium and in the Liver Acinus; The Journal of Biological Chemistry; vol. 268, No. 24, Aug. 25, 1993, p. 18345-18358.
Shin, Jordan T., From Zebrafish to Human: Modular Models; Annu. Rev. Genomics Hum. Genet.; vol. 3, p. 311-340, 2002.
Grunwald, David J., Headwaters of the zebrafish—emergence of a new model vertebrate; Perspectives; vol. 3, p. 717-724, Sep. 2002.
Briggs, Josephine P., The zebrafish: a new model organism for integrative physiology; Am J Physiol Regulatory Integrative Comp Physiol, vol. 282, p. R3-R9, 2002.
Zon, Leonard I., Zebrafish: A New Model for Human Disease; Insight/Outlook, vol. 9, p. 99-100, 1999.
Amatruda, James F., Zebrafish as a cancer model system; Cancer Cell, vol. 1, p. 229-231, Apr. 2002.
Langenau, David M., Myc-Induced T Cell Leukemia in Transgenic Zebrafish; Science, vol. 299, p. 887-890, Feb. 2003.
Her, Guor M., In vivo studies of liver-type fatty acid binding protein (L-FABP) gene expression in liver of transgenic zebrafish (Danio rerio); FEBS Letters, vol. 538, p. 125-133, 2003.

* cited by examiner

*Primary Examiner*—Celine Qian
*Assistant Examiner*—Laura M Mitchell
(74) *Attorney, Agent, or Firm*—Fei-Fei Chao; Andrews Kurth LLP

(57) ABSTRACT

The present invention relates to expression control sequences of a vertebrate liver fatty acid binding protein (L-FABP) gene that, when operably linked to a reporter (e.g., a heterologous reporter, such as the green fluorescent protein (GFP)), directly express the reporter in a fashion that mimics the liver-specific development of the L-FABP gene in the vertebrate.

5 Claims, 14 Drawing Sheets

```
gcagtaaatt gattcaaact gaaatcactg caaaatgatt ctaatagtaa atgcaaattc
tgagcaaatg actgaatata cactctccgg ccacttcatt aggtacacct gtccaactgc
tcattaatgc aaatttctaa tcaaccactc acatggcagc aactcaatgc attaaggtac
gtagacatgg tcaagacgat ctgctgcagt tcaaactgag catcagaatg gggaaggaag
aggatttcag tgactttgaa cgaggcatgg ttgttgctgc cggatgggct gctctgagta
tttcagaaac tgctgatctt cagggatttt cacgcacaac catctctagg gtttacagag
aatgatctga aaagaggaaa tatccagtga gcggcagttc tgtgggtgca aatgccttgt
tgatgccaga gatcagagga gaatggccag actggttcca gctgatagaa aggcaacagt
aactcaaata agcactcgtt acaaccgagc tctgcagaag agcatctctg aacacacaac
acgtccaacc ttgaggcaga tgggctacag cagcagaaga ccacaccggg tgccgctcct
gtcagctaag aacaggaaac tgaggctaca attcacacag actcaccaaa actggacatt
tattattagc ccccttaga attttcatt tgataatatt tttcttctgg cgaaagcctc
atttgtttta tatattatag aataaaatta gttttaata gttttatgc catttaagg
tcaatattat tagccccttt aagctatttt ttttcgatag tctacagaac aaaccatcgg
tatacaatga cttgcctaat taccctaacc tgcctagtta ccctaattaa cctagttaag
cctttaaatg tcactttaag ctgtatagaa gtgtcttgaa gaatatctag tctaatatta
ttgactgtca tcatggcaaa gataaaataa atcagttatt aaaactatta tgattagaaa
tgtgctgaaa caatctgctc tccgataaac agaaattgaa caaaataaac aggggggcta
ataaatttaa ggggttaaat aattctgatt gcaaaaaaaa tgatgtctgc aaaactgttg
caaataattt atttgtgttg attttaagca aacaattaa atttaataaa atacaactta
atctgtttgt ttaaattcag ccctaataaa ttgtttacag ccacttaacg taaaaaaatt
gagtaaatcc aaggaatcat ctctgaataa ttttttcagt gtatatatat atatatatat
tcttacaaaa caactcattt actttagtta attttcaggg gcaaaaacta aagtaatcga
cgttgcttga ataaaagtg taattaaggg aatgaggtaa catttaacca tgtgtcaatg
cagtttaaat atgccagtta gtggtatatg tttaaatggt aagctattca aaactttaaa
ctaacttaac cagcctttg ttgtcagact gaacagactt ccatctgca ttattagaga
ctaatctttg gctggatgaa tgattcatct gctgatattt cagaatagac agattgaggc
tgtttctaat atgattatgc aacctgaggg tgattatttg aagcaaactc cacagaccag
caggtcattg accgtcgtgt gttcaaacag agcagaaaca tttgcaaaac tggtctgaca
ggagaatcca gtccagcaca acacatatgc tgagcaaact gaatcaatcc tgcaggtcaa
ctctcgtgct ttaagtttat taaagattat tttatttatt tattatttta tttatctatt
tatttatta gttgtttatt tattcctgca gatcatgcct tgtgccttt tacatttaat
ttaatttta atttaatttc ctttatttt ttttatttt ttatttat tttatttac
agtctgacaa atactgaact aaaaacctct cagatcatgt ctatgcattt catttatttt
tatttcattt tatattatta atttaatat ttttatttta cagtctgaca aatactgaat
taaaaaccat cagatcatgt ctcatgcatt taacttaact ttatttaatt caattaaatt
gtttgtttgt ttgtttcctt gcatttgttt gtttgtttt tacaatctga catactggac
cgaaaaaact cagatcatgt cttatgcatt ttacttttat tttattagaa ttagaaagat
caaaggaaca actttaaaa tattaattct gtatcaaaat ctcttttgat acatttaatt
gatttaaaaa agcagttcac ccaagaaaca tttcctcaca gtcgaatggt tgtaaacttt
tatgaattac tttcacagaa aaagattttt ggaagaatat tggaaaaaaa gcagccattg
acttccatag taacaacaaa aaatactatg gaagtcaatg gctgtttttt caccattcgg
tatcttcatt ctggagcaga atttttggg tgacgagtct ttatttttgg tctgctactg
ctgtgtgtgt gagggcattt tgatctgtcc ctttaagtcg tcaaatcctg gtgcaatatt
ccacatgcac acctcatctt ctgctggagt tgatgaacgg tgggttgttc aaacagcagc
aggtcattga ctgaactcct ctcgatataa aagctgcaga tctgaagctg accttcactt
tgtgttgagc ttctccagaa agcatggcct tcagcgggac gtggcaggtt tacgctcagg
agaactacga ggagtttctc agagccatct ctctgccaga agaggtcatt aaactggcca
aagatgtgaa gccagtgaca gaaatccagc agaacggcag cgacttcacc atcacctcca
aaactcctgg aaaaaccgtc
```

Figure 6

```
-863  TTAATTTTTA ATTAATTTC CTTTTATTTT TT TTTATTTT  TTTATTTTAT AGTCTGACAA ATACTGAACT
                                         Cdx-2
-783  AAAAACCTCT CAGATCATGT CTATGCATTT C ATTTATTT TATTTCATT  TATATTATTA ATT TAATAT  TTTTATTTTA CAATTAAATT
                                         Cdx-2  Cdx-2                              Cdx-2
-703  CAG TCTGACA AATACTGAAT TAAAAACCAT CAGATCATGT CTCATGCATT TAACTTAACT CATACTCGAC CGAAAAAAACT CAGATCATGT
-623  GTTTGTTTGT TTGTTTCCTT GCATTTGTTT GTTTGTTTT TACAATCTGA CATACTGGAC CGAAAAAAACT GTATCAAAAT
-543  CTTATGCATT TTACTTTTTAT TTAGAAAGAT CAAAGCAACA ACTTTTAAAA TATTAATTCT GTATCAAAAT
              Cdx-2                                          Cdx-2
-463  CTCTTTTTGAT ACATTTAATT GATTTAAAAA AGCAACTTAC CCAAGAAACA TTTCCTACCA GTCGAATGGT T GTAAACTTT TAACAAACAAA
                                                                                    Cdx-2
-383  TATGAATTAC TTTCACAGAA AAAGATTTTT GGAAGAAATAT TGGAAAAAAAA  G CAGCCATTG ACTTCCATAC TAACAAACAAA
      TATA-Box                                                   CCAAT-Box
-303  AAATACTATC GAAGTCAAATG GCTCTTTTTT TATCTTCATT CTGGAGCAGA ATTTTTTGGG TGACGAGTCT
-223  TTATTTTGG TCTGCTACTC CTGTCTGTGT GAGGGCATTT TGATCTGTCC CTTTAAGTCG TCAAATCCTG GTGCAATATT
-143  CCACATGCAC ACCTCATCTT CTGTGAAGT TGATGAACGG TGGGTTGTTC AAACAGCAGC AGGTCATTGA CTGAACTCCT
-63   CTCGA ATATAC C TG GCAGA TCTGAAGCTG ACCTTCACTT TGTGTTGAGC TTCCCAGAA AGCATGGCCT TCAGCGGGAC
      TATA-Box                                                         +1
+18   GTGGCAGGTT TACCCTCAGG AGAACTACGA GGAGTTTCTC AGACCCATCT CTCTGCCAGA AGAGGTCATT AAACTGGCCA
+98   AAGATGTGAA GCCAGTGACA GAAACCGCAG AGAACGGCAG CCGACTTCACC AAACTCCTCC ATCCACCTCA AAAAACCGTC
+178  ACCAACTCCT TCACCATCGG CAAAGAGGCT GAAATCACCA CCATGG
```

Figure 7

Liver regulatory element

```
-1983 AAGCTATTTT TTTTCGATAG TCTACAGAAC AAACCATCGG TATACAATGA CTTGCCTAATAACCCTAACC TGCCTAGTTA
                                                                    PDX1/ISL1(1)
-1903 CCCTAATAA CCTAGTTAAG CCTTTAAATG TCACTTTAAG CTGTATAGAA GTGTCTTGAA GAATATCTAG TCTAATATTA
       PDX1/ISL1(2)
-1823 TTGACTGTCA TCATGGCAAA GATAAAATAA ATCAGTTATT AAAACTATTA TGATTAGAAA TGTGCTGAAA CAATCTGCTC
-1743 TCGTAATATG AGAAATTGAA CAAATTTATA AGGCGGGCTA ATAAATTTAA GGGGTTAAAT AATTCTGATT GCAAAAAAAA
       HFH(1)                HFH(2)
-1663 TGATGTCTGC AAAACTGTTG CAAATTAATTG TGTTG ATTTTAAGGAACAAATTAA ATTTAATAAA ATACAACTTA
                             HNF1-α                HNF3β
-1583 ATCTGTTTGT TTAAATTCAG CCCTAATAAA TTGTTTACAG CCACTTAACG TAAAAAAATT GAGTAAATCC AAGGAATCAT

-1510
                                                                         (SEQ ID NO:1)
```

REPLACEMENT Figure 11

SEQUENCE LISTING

<160> NUMBER OF SEQ ID NOS: 30

<210> SEQ ID NO 1
<211> LENGTH: 435
<212> TYPE: DNA
<213> ORGANISM: Danio rerio

<400> SEQUENCE: 1

```
gtatacaatg acttgcctaa ttaccctaac ctgcctagtt accctaatta acctagttaa      60
gcctttaaat gtcactttaa gctgtataga agtgtcttga agaatatcta gtctaatatt     120
attgactgtc atcatggcaa agataaaata aatcagttat taaaactatt atgattagaa     180
atgtgctgaa acaatctgct ctccgataaa cagaaattga acaaaataaa caggggggct     240
aataaattta agggttaaa taattctgat tgcaaaaaaa atgatgtctg caaaactgtt     300
gcaaataatt tatttgtgtt gattttaagc aaacaaatta aatttaataa aatacaactt     360
aatctgtttg tttaaattca gccctaataa attgtttaca gccacttaac gtaaaaaaat     420
tgagtaaatc caagg                                                     435
```

<210> SEQ ID NO 2
<211> LENGTH: 2783
<212> TYPE: DNA
<213> ORGANISM: Danio rerio

<400> SEQUENCE: 2

```
gcagtaaatt gattcaaact gaaatcactg caaaatgatt ctaatagtaa atgcaaattc      60
tgagcaaatg actgaatata cactctccgg ccacttcatt aggtacacct gtccaactgc     120
tcattaatgc aaatttctaa tcaaccactc acatggcagc aactcaatgc attaaggtac     180
gtagacatgg tcaagacgat ctgctgcagt tcaaactgag catcagaatg gggaaggaag     240
aggatttcag tgactttgaa cgaggcatgg ttgttgctgc cggatgggct gctctgagta     300
tttcagaaac tgctgatctt cagggatttt cacgcacaac catctctagg gtttacagag     360
aatgatctga aaagaggaaa tatccagtga gcggcagttc tgtgggtgca aatgccttgt     420
tgatgccaga gatcagagga gaatggccag actggttcca gctgatagaa aggcaacagt     480
aactcaaata agcactcgtt acaaccgagc tctgcagaag agcatctctg aacacacaac     540
```

```
acgtccaacc ttgaggcaga tgggctacag cagcagaaga ccacaccggg tgccgctcct      600
gtcagctaag aacaggaaac tgaggctaca attcacacag actcaccaaa actggacatt      660
tattattagc cccccttaga attttttcatt tgataatatt tttcttctgg cgaaagcctc     720
atttgtttta tatattatag aataaaatta gttttaata gttttatgc cattttaagg        780
tcaatattat tagccccttt aagctatttt ttttcgatag tctacagaac aaaccatcgg      840
tatacaatga cttgcctaat taccctaacc tgcctagtta ccctaattaa cctagttaag      900
cctttaaatg tcactttaag ctgtatagaa gtgtcttgaa gaatatctag tctaatatta      960
ttgactgtca tcatggcaaa gataaaataa atcagttatt aaaactatta tgattagaaa     1020
tgtgctgaaa caatctgctc tccgataaac agaaattgaa caaaataaac agggggcta      1080
ataaatttaa ggggttaaat aattctgatt gcaaaaaaaa tgatgtctgc aaaactgttg     1140
caaataattt atttgtgttg attttaagca aacaaattaa atttaataaa atacaactta     1200
atctgtttgt ttaaattcag ccctaataaa ttgtttacag ccacttaacg taaaaaaatt     1260
gagtaaatcc aaggaatcat ctctgaataa ttttttcagt gtatatatat atatatatat     1320
tcttacaaaa caactcattt actttagtta attttcaggg gcaaaaacta aagtaatcga     1380
cgttgcttga ataaaaagtg taattaaggg aatgaggtaa catttaacca tgtgtcaatg     1440
cagtttaaat atgccagtta gtggtatatg tttaaatggt aagctattca aaactttaaa     1500
ctaacttaac cagccttttg ttgtcagact gaacagactt tccatctgca ttattagaga     1560
ctaatctttg gctggatgaa tgattcatct gctgatattt cagaatagac agattgaggc     1620
tgtttctaat atgattatgc aacctgaggg tgattatttg aagcaaactc cacagaccag     1680
caggtcattg accgtcgtgt gttcaaacag agcagaaaca tttgcaaaac tggtctgaca     1740
ggagaatcca gtccagcaca acacatatgc tgagcaaact gaatcaatcc tgcaggtcaa     1800
ctctcgtgct ttaagtttat taaagattat tttatttatt tattattttta tttatctatt    1860
tatttattta gttgtttatt tattcctgca gatcatgcct tgtgcctttt tacatttaat     1920
ttaatttta atttaatttc cttttatttt tttttattttt tttatttttat tttatttttac  1980
agtctgacaa atactgaact aaaaacctct cagatcatgt ctatgcattt cattttattt     2040
tatttcattt tatattatta attttaatat ttttattttta cagtctgaca aatactgaat    2100
taaaaaccat cagatcatgt ctcatgcatt taacttaact ttatttaatt caattaaatt     2160
gtttgtttgt ttgtttcctt gcatttgttt gtttgttttt tacaatctga catactggac     2220
cgaaaaaact cagatcatgt cttatgcatt ttactttat tttattagaa ttagaaagat      2280
caaaggaaca acttttaaaa tattaattct gtatcaaaat ctcttttgat acatttaatt     2340
gatttaaaaa agcagttcac ccaagaaaca tttcctcaca gtcgaatggt tgtaaacttt     2400
tatgaattac tttcacagaa aaagattttt ggaagaatat tggaaaaaaa gcagccattg     2460
acttccatag taacaacaaa aaatactatg gaagtcaatg gctgtttttt caccattcgg     2520
tatcttcatt ctggagcaga atttttggg tgacgagtct ttattttgg tctgctactg       2580
ctgtgtgtgt gagggcattt tgatctgtcc ctttaagtcg tcaaatcctg gtgcaatatt     2640
ccacatgcac acctcatctt ctgctggagt tgatgaacgg tgggttgttc aaacagcagc     2700
aggtcattga ctgaactcct ctcgatataa agctgcaga tctgaagctg accttcactt      2760
tgtgttgagc ttctccagaa agc                                             2783
```

<210> SEQ ID NO 3
<211> LENGTH: 2033

<212> TYPE: DNA
<213> ORGANISM: Danio rerio

<400> SEQUENCE: 3

```
gtttttaata gtttttatgc catttttaagg tcaatattat tagccccttt aagctatttt      60
ttttcgatag tctacagaac aaaccatcgg tatacaatga cttgcctaat taccctaacc     120
tgcctagtta ccctaattaa cctagttaag cctttaaatg tcactttaag ctgtatagaa     180
gtgtcttgaa gaatatctag tctaatatta ttgactgtca tcatggcaaa gataaaataa     240
atcagttatt aaaactatta tgattagaaa tgtgctgaaa caatctgctc tccgataaac     300
agaaattgaa caaaataaac agggggcta ataaatttaa ggggttaaat aattctgatt      360
gcaaaaaaaa tgatgtctgc aaaactgttg caaataattt atttgtgttg attttaagca     420
aacaaattaa atttaataaa atacaactta atctgtttgt ttaaattcag ccctaataaa     480
ttgtttacag ccacttaacg taaaaaaatt gagtaaatcc aaggaatcat ctctgaataa     540
ttttttcagt gtatatatat atatatatat tcttacaaaa caactcattt actttagtta     600
attttcaggg gcaaaaacta aagtaatcga cgttgcttga ataaaaagtg taattaaggg     660
aatgaggtaa catttaacca tgtgtcaatg cagtttaaat atgccagtta gtggtatatg     720
tttaaatggt aagctattca aaactttaaa ctaacttaac cagcctttg ttgtcagact      780
gaacagactt tccatctgca ttattagaga ctaatctttg gctggatgaa tgattcatct     840
gctgatattt cagaatagac agattgaggc tgtttctaat atgattatgc aacctgaggg     900
tgattatttg aagcaaactc cacagaccag caggtcattg accgtcgtgt gttcaaacag     960
agcagaaaca tttgcaaaac tggtctgaca ggagaatcca gtccagcaca acacatatgc    1020
tgagcaaact gaatcaatcc tgcaggtcaa ctctcgtgct ttaagtttat taagagattat    1080
tttatttatt tattatttta tttatctatt tatttattta gttgtttatt tattcctgca    1140
gatcatgcct tgtgccttt tacatttaat ttaattttta atttaatttc ctttttatttt     1200
ttttatttt tttattttat tttattttac agtctgacaa atactgaact aaaaaccctct     1260
cagatcatgt ctatgcattt cattttattt tatttcattt tatattatta atttaatat     1320
ttttatttta cagtctgaca aatactgaat taaaaccat cagatcatgt ctcatgcatt     1380
taacttaact ttatttaatt caattaaatt gtttgtttgt ttgttccctt gcatttgttt     1440
gtttgtttt tacaatctga catactggac cgaaaaaact cagatcatgt cttatgcatt     1500
ttacttttat tttattagaa ttagaaagat caaaggaaca acttttaaaa tattaattct    1560
gtatcaaaat ctcttttgat acatttaatt gatttaaaaa agcagttcac ccaagaaaca    1620
tttcctcaca gtcgaatggt tgtaaacttt tatgaattac tttcacagaa aaagattttt    1680
ggaagaatat tggaaaaaaa gcagccattg acttccatag taacaacaaa aaatactatg    1740
gaagtcaatg gctgtttttt caccattcgg tatcttcatt ctggagcaga atttttt ggg    1800
tgacgagtct ttattttttgg tctgctactg ctgtgtgtgt gagggcattt tgatctgtcc    1860
ctttaagtcg tcaaatcctg gtgcaatatt ccacatgcac acctcatctt ctgctggagt    1920
tgatgaacgg tgggttgttc aaacagcagc aggtcattga ctgaactcct ctcgatataa    1980
aagctgcaga tctgaagctg accttcactt tgtgttgagc ttctccagaa agc           2033
```

<210> SEQ ID NO 4
<211> LENGTH: 14
<212> TYPE: DNA
<213> ORGANISM: Danio rerio

```
<400> SEQUENCE: 4
tccgataaac agaa                                                     14

<210> SEQ ID NO 5
<211> LENGTH: 13
<212> TYPE: DNA
<213> ORGANISM: Danio rerio

<400> SEQUENCE: 5
aaaataaaca ggg                                                      13

<210> SEQ ID NO 6
<211> LENGTH: 15
<212> TYPE: DNA
<213> ORGANISM: Danio rerio

<400> SEQUENCE: 6
aatttatttg tgttg                                                    15

<210> SEQ ID NO 7
<211> LENGTH: 20
<212> TYPE: DNA
<213> ORGANISM: Danio rerio

<400> SEQUENCE: 7
attttaagca aacaaattaa                                               20

<210> SEQ ID NO 8
<211> LENGTH: 21
<212> TYPE: DNA
<213> ORGANISM: Danio rerio

<400> SEQUENCE: 8
tgacttgcct aattaccta a                                              21

<210> SEQ ID NO 9
<211> LENGTH: 20
<212> TYPE: DNA
<213> ORGANISM: Danio rerio

<400> SEQUENCE: 9 tagttacccct aattaaccta                                              20

<210> SEQ ID NO 10
<211> LENGTH: 24
<212> TYPE: DNA
<213> ORGANISM: artificial sequence
<220> FEATURE:
<223> OTHER INFORMATION: primer LF-1

<400> SEQUENCE: 10
caaagatgtg aagccagtga caga                                          24

<210> SEQ ID NO 11
<211> LENGTH: 24
<212> TYPE: DNA
<213> ORGANISM: artificial sequence
<220> FEATURE:
<223> OTHER INFORMATION: primer LF-2

<400> SEQUENCE: 11
tttaatgacc tcttctggca gaga                                          24
```

<210> SEQ ID NO 12
<211> LENGTH: 32
<212> TYPE: DNA
<213> ORGANISM: artificial sequence
<220> FEATURE:
<223> OTHER INFORMATION: primer for L-FABP (forward)

<400> SEQUENCE: 12
gctctagaat gaagagatac cagtgtctgt tc                32

<210> SEQ ID NO 13
<211> LENGTH: 33
<212> TYPE: DNA
<213> ORGANISM: artificial sequence
<220> FEATURE:
<223> OTHER INFORMATION: primer for L-FABP (reverse)

<400> SEQUENCE: 13
ccgctcgagt ttgtcgtgac cccggatgtg gct               33

<210> SEQ ID NO 14
<211> LENGTH: 21
<212> TYPE: DNA
<213> ORGANISM: artificial sequence
<220> FEATURE:
<223> OTHER INFORMATION: primer for beta-actin (forward)

<400> SEQUENCE: 14
gtccctgtac gcctctggtc g                            21

<210> SEQ ID NO 15
<211> LENGTH: 21
<212> TYPE: DNA
<213> ORGANISM: artificial sequence
<220> FEATURE:
<223> OTHER INFORMATION: primer for beta-actin (reverse)

<400> SEQUENCE: 15
gccggactca tcgtactcct g                            21

<210> SEQ ID NO 16
<211> LENGTH: 25
<212> TYPE: DNA
<213> ORGANISM: artificial sequence
<220> FEATURE:
<223> OTHER INFORMATION: hhex MO sequence

<400> SEQUENCE: 16
gcgcgtgcgg gtgctggaat tgcat                        25

<210> SEQ ID NO 17
<211> LENGTH: 25
<212> TYPE: DNA
<213> ORGANISM: artificial sequence
<220> FEATURE:
<223> OTHER INFORMATION: zXbp-1 MO sequence

<400> SEQUENCE: 17
cggtccctgc tgtaactacg accat                        25

<210> SEQ ID NO 18
<211> LENGTH: 20
<212> TYPE: DNA
<213> ORGANISM: artificial sequence
<220> FEATURE:
<223> OTHER INFORMATION: 3' end primer for pLF2.5-EGFP, pLF2.0-EGFP,
      pLF1.8-EGFP, pLF1.5-EGFP, pLF1.2-EGFP, pLF1.0-EGFP, pLF0.8-EGFP and pLF0.5-EGFP

<400> SEQUENCE: 18
aacactcaac cctatctcgg                                          20

<210> SEQ ID NO 19
<211> LENGTH: 20
<212> TYPE: DNA
<213> ORGANISM: artificial sequence
<220> FEATURE:
<223> OTHER INFORMATION: 5' end primer for pLF2.5-EGFP

<400> SEQUENCE: 19
cggatgggct gctctgagta                                          20

<210> SEQ ID NO 20
<211> LENGTH: 20
<212> TYPE: DNA
<213> ORGANISM: artificial sequence
<220> FEATURE:
<223> OTHER INFORMATION: 5' end primer for pLF2.0-EGFP

<400> SEQUENCE: 20
aaggtcaata ttattagccc                                          20

<210> SEQ ID NO 21
<211> LENGTH: 20
<212> TYPE: DNA
<213> ORGANISM: artificial sequence
<220> FEATURE:
<223> OTHER INFORMATION: 5' end primer for pLF1.8-EGFP

<400> SEQUENCE: 21
tgtgctgaaa caatctgctc                                          20

<210> SEQ ID NO 22
<211> LENGTH: 20
<212> TYPE: DNA
<213> ORGANISM: artificial sequence
<220> FEATURE:
<223> OTHER INFORMATION: 5' end primer for pLF1.5-EGFP

<400> SEQUENCE: 22
ctctgaataa ttttttcagt                                          20

<210> SEQ ID NO 23
<211> LENGTH: 20
<212> TYPE: DNA
<213> ORGANISM: artificial sequence
<220> FEATURE:
<223> OTHER INFORMATION: 5' end primer for pLF1.2-EGFP

<400> SEQUENCE: 23
ttattagaga ctaatctttg                                          20

<210> SEQ ID NO 24
<211> LENGTH: 20
<212> TYPE: DNA
<213> ORGANISM: artificial sequence
<220> FEATURE:
<223> OTHER INFORMATION: 5' end primer for pLF1.0-EGFP

<400> SEQUENCE: 24
gaatcaatcc tgcaggtcaa                                          20

```
<210> SEQ ID NO 25
<211> LENGTH: 20
<212> TYPE: DNA
<213> ORGANISM: artificial sequence
<220> FEATURE:
<223> OTHER INFORMATION: 5' end primer for pLF0.8-EGFP

<400> SEQUENCE: 25
cagatcatgt ctatgcattt                                                 20

<210> SEQ ID NO 26
<211> LENGTH: 20
<212> TYPE: DNA
<213> ORGANISM: artificial sequence
<220> FEATURE:
<223> OTHER INFORMATION: 5' end primer for pLF0.5-EGFP

<400> SEQUENCE: 26
gtatcaaaat ctcttttgat                                                 20

<210> SEQ ID NO 27
<211> LENGTH: 1086
<212> TYPE: DNA
<213> ORGANISM: Danio rerio

<400> SEQUENCE: 27 ttaatttta atttaatttc cttttatttt tttttatttt tttattttat tttattttac      60
agtctgacaa atactgaact aaaaacctct cagatcatgt ctatgcattt cattttattt    120
tatttcattt tatattatta atttttaatat ttttatttta cagtctgaca atactgaat    180 taaaaaccat cagatcatgt ctcatgcatt taacttaact ttatttaatt caattaaatt    240
gtttgtttgt ttgtttcctt gcatttgttt gtttgttttt tacaatctga catactggac    300
cgaaaaaact cagatcatgt cttatgcatt ttacttttat tttattagaa ttagaaagat    360
caaaggaaca acttttaaaa tattaattct gtatcaaaat ctcttttgat acatttaatt    420
gatttaaaaa agcagttcac ccaagaaaca tttcctcaca gtcgaatggt tgtaaacttt    480
tatgaattac tttcacagaa aaagattttt ggaagaatat tggaaaaaaa gcagccattg    540
acttccatag taacaacaaa aaatactatg gaagtcaatg gctgttttttt caccattcgg    600 tatcttcatt ctggagcaga attttttggg tgacgagtct ttattttttgg tctgctactg    660 ctgtgtgtgt gagggcattt tgatctgtcc ctttaagtcg tcaaatcctg gtgcaatatt    720
ccacatgcac acctcatctt ctgctggagt tgatgaacgg tgggttgttc aaacagcagc    780
aggtcattga ctgaactcct ctcgatataa aagctgcaga tctgaagctg accttcactt    840
tgtgttgagc ttctccagaa agcatggcct tcagcgggac gtggcaggtt tacgctcagg    900
agaactacga ggagtttctc agagccatct ctctgccaga agaggtcatt aaactggcca    960
aagatgtgaa gccagtgaca gaaatccagc agaacggcag cgacttcacc atcacctcca   1020
aaactcctgg aaaaaccgtc accaactcct tcaccatcgg caaagaggct gaaatcacca   1080
ccatgg                                                              1086

<210> SEQ ID NO 28
<211> LENGTH: 486
<212> TYPE: DNA
<213> ORGANISM: Rattus norvegicus

<400> SEQUENCE: 28
aaagatccta ggctttcccc cttccctctt ttctgccctc ttcctttcct tcatttctac     60
```

-continued

```
cttttagctg ttattttaag caccatgtcg atactagcta gtatgctacc atgttggact      120
agctcttata ttagttagtt agtattgtac catgttggac tagctcttat attagttagt      180
tagtattgta ccatgttgga ctagctctta tattagttag ttagtattgt accatgttgg      240
actagctctt atattagtta gttagtattg taccatgttg gactagctct tatattagtt      300
agttagtatt gtaccatgtt ggactagctc ttctattagt tagttagtat tgtaccatgt      360
tggactagct cttatattag ttagttagta tgctaccatg ttggactagc tcttctatta      420
gttagttagt atgctaccat gctggactag ctctttggac aggtggtaga tgaaaagggc      480
tgaatg                                                                 486

<210> SEQ ID NO 29
<211> LENGTH: 453
<212> TYPE: DNA
<213> ORGANISM: Mus musculus

<400> SEQUENCE: 29
ccatatacaa gtgtgcacat gtacaaacac atacatatgt gcacttaggt atatatgcat       60
atgtgcattg ctggagatgt gattcacatg tttctaaatt atttctaaat gtattgatgt      120
tgcacataca tacatttgtc aacatacatt tcaaccatgc acacttattt catgagtagg      180
gttaagtcac cataaaggca acatttacag agagctttgc ccttggttgg actcactaat      240
gtttgctgaa ttagaacaaa cctctgcctt gcccactctg attttatcg ttgaccattg       300 ctctcaggag ttaatgtttg agcctggcca taaataaatt cgacaatcac tgacctatgg      360
cctatattcg aggaggaaga atccccttat aaaataggca acagtgggtg acctggcagg      420
cagagctgtt gtggtcagct gtggaaagga aac                                   453

<210> SEQ ID NO 30
<211> LENGTH: 480
<212> TYPE: DNA
<213> ORGANISM: Danio rerio

<400> SEQUENCE: 30 aagctattt ttttcgatag tctacagaac aaaccatcgg tatacaatga cttgcctaat        60
taccctaacc tgcctagtta ccctaattaa cctagttaag cctttaaatg tcactttaag      120
ctgtatagaa gtgtcttgaa gaatatctag tctaatatta ttgactgtca tcatggcaaa      180
gataaaataa atcagttatt aaaactatta tgattagaaa tgtgctgaaa caatctgctc      240
tccgataaac agaaattgaa caaaataaac agggggggcta ataaatttaa ggggttaaat    300
aattctgatt gcaaaaaaaa tgatgtctgc aaaactgttg caaataattt atttgtgttg     360
attttaagca aacaaattaa atttaataaa atacaactta atctgtttgt ttaaattcag     420
ccctaataaa ttgtttacag ccacttaacg taaaaaaatt gagtaaatcc aaggaatcat     480
```

TRANSGENIC FISH GERMLINE EXPRESSION DRIVEN BY LIVER FATTY ACID BINDING (L-FABP) GENE PROMOTER AND APPLICATIONS THEREOF

RELATED APPLICATION

This application claims U.S. provisional application Ser. No. 60/463,035, filed on Apr. 16, 2003, and U.S. provisional application Ser. No. 60/473,210, filed on May 27, 2003, which are herein incorporated by reference.

FIELD OF THE INVENTION

The present invention relates to an expression control sequence or a variant thereof having at least 90% homology to the expression control sequence. The expression control sequence modulates a vertebrate liver fatty acid binding protein (L-FABP) gene in liver of the vertebrate. The preferred expression control sequence is a 435 bp nucleic acid sequence isolated from zebrafish, which is situated upstream from the gene of zebrafish L-FABP. The expression control sequence, when operably linked to a reporter (e.g., a heterologous reporter, such as the green fluorescent protein (GFP)), expresses the reporter in a fashion that mimics the liver-specific development of the L-FABP gene in the vertebrate. Also disclosed is a transgenic fish, particularly a transgenic zebrafish, whose cells comprises at least one genomically integrated copy of a recombinant construct comprising such an expression control sequence, operably linked to a reporter, so that the expression of the reporter is liver-cell specific, both spatially and temporally during the development of the fish. The transgenic zebrafish can be used as models for the study of liver development, drug screening and/or biomedical research.

BACKGROUND INFORMATION

The liver fatty acid binding protein (L-FABP) of zebrafish is a 14-kD cytoplasmic protein that binds long-chain fatty acids (LCFAs) with high affinity. The putative functions assigned to L-FABP include the desorption of LCFAs from the plasma membrane to the cytoplasm, the promotion of intracellular fatty acid (FA) diffusion, the targeting of FAs to different metabolic pathways, and protection against the cytotoxic effects of free FA. Three FABP types have been found in zebrafish organs/tissues: intestinal-type FABP (I-FABP), brain-type FABP (B-FABP), and liver-type FABP (L-FABP). The zebrafish FABPs were originally named according to their site of initial isolation. The zebrafish I-FABP is uniformly expressed throughout the intestine. The zebrafish B-FABP mRNA is expressed in the periventricular gray zone of the optic tectum of the adult zebrafish brain. The L-FABP is expressed exclusively in the liver of the adult zebrafish.

FABPs are found in other vertebrates as well, for example, in mice, rats and humans. Three homologous genes encode FABPs in mice: mouse liver fatty acid-binding protein (L-FABP, or Fabpl), intestinal fatty acid-binding protein (I-FABP, or Fabpi), and ileal lipid binding protein (Ilbp). Mouse, rat, and human L-FABP are transcribed in the liver (hepatocytes) and intestines (postmitotic, differentiating members of the enterocytic lineage), in contrast to zebrafish, in which L-FABP is expressed solely in the liver. The study of mouse and rat L-FABP has been used as a model for understanding the mechanisms that determine distinct regional expression along the gut tube, as well as within the liver. As in zebrafish, L-FABP is thought to play a pivotal role in other vertebrates in the intracellular binding and trafficking of fatty acids in the liver. The importance of L-FABP in vertebrate physiology is underscored by the fact that L-FABP mRNA constitutes 1.6% of translatable RNA of adult male rat livers and accounts for 3 to 5% of the cytosolic protein mass in rat hepatocytes.

Zebrafish have been used extensively to study vertebrate embryonic development, yielding insights into the formation and function of individual tissues, organ systems and neural networks. Transgenic zebrafish, which express transgenes under the control of either zebrafish or heterologous expression control sequences, have been particularly useful in this regard. Zebrafish comprising transgenes, mutant genes, or genes whose expression is altered in some other fashion, can also serve as model systems for diseases in other vertebrates, including humans, and can provide insight into disease mechanisms. Review articles summarizing the use of zebrafish as disease models include Shin et al. (2002), *Ann Rev Genomics Hum Genet* 3, 311-40; Grunwald et al. (2002), *Nature Reviews/Genetics* 3, 717-724; Briggs et al. (2002), *Am J Physiol Regulatory Comp Physiol* 282, R3-R9; Zon (1999), *Genome Research* 9, 99-100; and Amatruda et al. (2002), *Cancer Cell* 1, 229-231, which are herein incorporated by reference.

In view of similarities in liver function and development between zebrafish and other vertebrates, it is expected that mutant zebrafish, including transgenic zebrafish, could serve as models for pathological studies of the liver in other vertebrates, including humans. At approximately 32 hpf, the zebrafish liver derives from the primitive gut tube as a morphologically distinct left ventrolateral diverticulum. Like its mammalian counterpart, the zebrafish liver produces bile, which is evident by 3 dpf under the dissecting microscope. Several zebrafish mutations with early liver degeneration have been isolated. For example, the *lumpazi, gammler,* and *tramp* mutations encode defects at three loci that lead to liver necrosis. The *beefeater* mutation shows liver necrosis and impaired glycogen utilization, as seen in the human glycogen storage diseases. Many different types of hepatic injury—e.g., alcohol, infection, and toxins—cause a similar pattern of histological degeneration and ultimately lead to cirrhosis. The pathways leading to massive liver failure are presently poorly understood. The only remedy currently available at such late stages in humans is transplantation of the liver.

Studies with zebrafish, particularly transgenic zebrafish, in which reporter genes are driven by liver-specific expression control sequences, would be useful for, e.g., the study of pathways involved in liver morphogenesis, for the study of disease conditions involving liver pathology, and as the basis for assays for modulatory agents, such as drug candidates or environmental mutagens.

SUMMARY OF THE INVENTION

The present invention provides an isolated polynucleotide, which contains a liver-specific expression control sequence. The expression control sequence can be a naturally existed nucleotide sequence, a recombinant nucleotide sequence, or a synthetic or semi-nucleotide sequence. It functions to modulate the gene expression of a vertebrate liver fatty acid binding protein (L-FABP). The preferred vertebrate is fish, preferably, zebrafish.

The expression control sequence contains 4 binding sites for liver-enriched transcriptional regulatory factors, which are HFH(1) having a nucleotide sequence of SEQ ID NO:4, HFH(2) having a nucleotide sequence of SEQ ID NO:5, HNF-1α having a nucleotide sequence of SEQ ID NO:6, and HNF-3β having a nucleotide sequence of SEQ ID NO:7. Optionally, additional binding sites such as binding site for PDX1 having a nucleotide sequence of SEQ ID NO:8, and/or binding site for PDX2 having a nucleotide sequence of SEQ ID NO:9 are included. The absence of either or both of the binding site sequences for PDX1 and/or PDX2 did not appear to have significant effects on the liver gene activity. However, the lack of the binding sites for HFH(1), HFH(2), HNF-1α, and/or HNF-3β affects significantly the gene activity in liver.

In one preferred embodiment, the expression control sequence contains a nucleic acid sequence of SEQ ID NO:1 (hereinafter "LR", which is a liver-specific regulatory sequence) or a variant thereof having at least 80% homology to the nucleic acid sequence of SEQ ID NO: 1. The nucleic acid sequence of SEQ ID NO:1 is isolated from the upstream region (between nucleotide −1944 and −1510) of the L-FABP gene in zebrafish. LR contains 435 bp. LR contains the 4 liver-specific binding sites for HFH(1), HFH(2), HNF-1α, and HNF-3β. LR further comprises the binding sites for PDX1, and/or PDX2, although the presence or absence of the binding sites for PDX1 and/or PDX2 does not affect the liver gene activity.

In another preferred embodiment, the expression control sequence contains a nucleic acid sequence of SEQ ID NO:2 (which is used interchangeably with "2.8 kb" sequence) or a variant thereof having at least 80% homology to the 2.8 kb sequence. The 2.8 kb sequence is located at the 5'flanking region of zebrafish, i.e., upstream from the L-FABP gene in a zebrafish at about nucleotide −2783 to −1. The 2.8 kb sequence contains a TATA-like sequence and two CAAT boxes, which suggest the inclusion of a core promoter for L-FABP. The LR is inclusive in the 2.8 kb sequence. Because of the inclusion of the LR, the 2.8 kb sequence also contains the 4 liver-specific binding sites for HFH(1), HFH(2), HNF-1α, and HNF-3β and optionally the binding sites for PDX1, and/or PDX2.

In yet another preferred embodiment, the expression control sequence contains a nucleic acid sequence of SEQ ID NO:3 (which is used interchangeably with "about 2.0 kb" sequence) or a variant thereof having at least 80% homology to the about 2.0 kb sequence. The about 2.0 kb sequence is isolated from the upstream region of the L-FABP gene (i.e., at nucleotide −2033 to −1). Like the 2.8 kb sequence, the about 2.0 kb sequence also includes the LR and a core promoter for L-FABP. Because of the inclusion of the LR, the about 2.0 kb sequence also contains the 4 liver-specific binding sites for HFH(1), HFH(2), HNF-1α, and HNF-3β and optionally the binding sites for PDX1, and/or PDX2.

The present invention also provides a recombinant construct which contains a basal promoter and the expression control sequence, is operably linked to a reporter sequence. The preferred reporter sequence encodes a green fluorescent protein (GFP). The nucleotide sequence that encodes the GFP can be a nature DNA sequence derived from *Aequorea victoria* or a mutant thereof. The preferred basal promoter used in the recombinant construct includes, but is not limited to, a core promoter for a vertebrate L-FABP gene, a SV40 promoter, a CMV promoter, or a RSV promoter.

In one embodiment, the recombinant construct is used for detecting L-FABP promoter activity in a eukaryotic cell by introducing the recombinant construct into the eukaryotic cell, and monitoring the expression of the reporter sequence in the cell.

In another embodiment, the recombinant construct is microinjected into an embryo of a fish, preferably zebrafish, to construct a transgenic fish. The transgenic fish is characterized to have at least one genomical copy of the recombinant construct integrated into the somatic and germ cells. The reporter sequence, which is operably linked to the expression control sequence, is expressed in the liver of the transgenic fish, indicating that the expression is liver-specific. The expression of the reporter sequence occurs both spatially and temporally during development of the transgenic fish.

The transgenic fish is produced by introducing the recombinant into a fish embryo, and allowing the embryo to develop into an adult fish. The recombinant construct is integrated into the genome of the zebrafish.

The transgenic zebrafish can be used as models to study drug or environmental agent effects on liver development by microinjecting the drug or agent to an embryo of the transgenic zebrafish which contains a reporter gene encoding a green fluorescent protein (GFP), allowing the zebrafish embryo to grow, while monitoring the liver development visually or under a fluorescent microscope. Zebrafish embryos are external and optically clear, which allows visual analysis of the development of internal structures and cells in living animals. In addition to visual monitoring of the transgenic zebrafish during the liver development, it is optional to isolate the hepatic cells to conduct in vitro analysis of the animals.

The transgenic zebrafish can also be used for detecting a gene that affects liver development by microinjecting a known inhibitor to a liver-specific gene to an embryo of the transgenic zebrafish which contains a reporter gene encoding a GFP, allowing the zebrafish embryo to grow, and monitoring said liver development during said development of said transgenic zebrafish visually or under a fluorescent microscope. An example of the inhibitor that affects the expression of a liver-specific gene and thus interrupts liver development is the morpholino antisense oligonucleotides, which target zebrafish Hex (hhex) and Xbp-1 (zXbp-1) mRNA to produce zebrafish morphants with liver phenotypes.

Finally, the transgenic zebrafish can be used as research tools for studies of liver cancer or other liver diseases in pharmaceutical and/or biomedical industry by microinjecting a mutagen to or UV-irradiating the transgenic zebrafish embryo which contains a reporter gene encoding a GFP, allowing the zebrafish embryo to grow, and selecting the mutant by monitoring the progression of the liver disease in the transgenic zebrafish visually or under a fluorescent microscope. An example of the liver disease is the mutations of the *lumpazi, gammler,* and *tramp* loci, which result in liver necrosis. Another example of the liver disease is the *beefeater* mutation, which results in liver necrosis due to impaired glycogen utilization, similar to human glycogen storage diseases.

BRIEF DESCRIPTION OF THE DRAWINGS

FIGS. 2A, C, E, G, I, L and N show in situ hybridization to detect endogenous L-FABP. Green fluorescence (GF) photomicrographs were obtained at various stages of transgenic zebrafish development (FIGS. 2B, D, F, H, M and O). Insets in FIGS. 2B, D, F, H, M and O show higher magnification images of the GFP-positive liver primordia. Confocal images are shown in FIGS. 2J and K. Scale bars: 50 μm (FIGS. 2A-I and 2L-O); 125 μm (FIGS. 2J, 2K); 50 μm (inserts).

FIG. 3A shows that the liver exhibited a conical shape at 9 dpf. FIGS. 3B and 3C show that the anterior end of the intestinal tube is surrounded by the liver in 9 dpf transgenic larvae. FIG. 3B show the dissected liver and intestine in the boxed region in FIG. 3A, depicted at higher power. FIG. 3C shows a cross-section of 9 dpf liver. FIG. 3D shows that the liver becomes a crescent-shaped structure at 14 dpf. Figure E shows the dissected liver in the boxed region in FIG. 3D, depicted at higher power. FIG. 3F shows a sagittal section of 14 dpf liver. The liver significantly increases its length in 14 dpf fish. Scale bars: 100 μm (FIGS. 3A, 3D; 50 μm (FIGS. 3B, 3E); 100 μm (FIGS. 3C, 3F).

FIGS. 4A-4D show that eGFP expression is strong in the juvenile (FIG. 4A: 20 dpf; FIG. 4B: 51 dpf) and adult zebrafish liver (FIG. 4C: 96 dpf; FIG. 4D: 4 months). FIG. 4E shows a sagittal cryosection of the liver from the 51 dpf transgenic fish in FIG. 4B; green fluorescence is only observed in the liver. FIG. 4F shows that individual GFP-labeled liver cells (hepatocytes) were clearly seen in the liver. FIG. 4G shows that GFP expression in liver is still quite detectable and there is no visible defect in the liver after 13 months of development. Lack of green fluorescence in a wild-type fish is shown for comparison. Scale bars: 0.2 cm (FIGS. 4A, B, E); 0.25 cm (FIG. 4C); 100 μm (FIG. 4F); 0.5 cm (FIGS. 4D, 4G).

FIGS. 5A-5C show the 4 dpf hhex morphant. FIGS. 5D-5F show the 4 dpf hhex control-injected morphant. FIG. 5A shows that the liver in the hhex morphant is much smaller than in hhex control-injected morphant (FIG. 5D). FIG. 5B shows the hhex morphant in FIG. 5A, depicted at low power. FIG. 5D shows that the liver of hhex control morphant is normal. FIG. 5E shows the hhex control morphant in FIG. 5D, depicted at low power. FIGS. 5C and 5F show histological cross-sections of 4 dpf hhex morphants and hhex control-injected embryos. FIG. 5C shows that interrupted liver development of hhex morphants was easily seen in the histological section. FIG. 5F shows that small amount of hepatic tissue in the hhex morphant (FIG. 5C) compared with the hhex control-injected morphant. FIGS. 5G-5I show the 4 dpf zXbp-1 morphant. FIGS. 5J-5L show the 4 dpf zXbp-1 control-injected morphant. FIG. 5G shows that the liver in the zXbp-1 morphant is little smaller than in zXbp-1 control-injected morphant (FIG. 5J). FIG. 5H shows the zXbp-1 morphant in FIG. 5G, depicted at low power. FIG. 5J shows that the liver of zXbp-1 control morphant is normal. FIG. 5K shows the zXbp-1 control morphant in FIG. 5J, depicted at low power. FIGS. 5I and 5L show histological cross-sections of the 4 dpf zXbp-1 morphant and zXbp-1 control-injected morphant. FIG. 5I shows that interrupted liver development of zXbp-1 morphant was easily seen in the histological section. FIG. 5L shows the low density of liver cells in ZXbp-1 morphants (FIG. 5I) compared with ZXbp-1 control-injected embryos. Scale bars: 50 μm (FIGS. 5A, D, G, J); 100 μm (FIGS. 5C, F, I, L). OV: otic vesicle; V: ventricle.

FIG. 6 shows the sequence of 2783 nucleotides upstream of the zebrafish L-FABP coding sequences, plus some coding sequences (Genbank Accession number AF512998). This is SEQ ID NO:2.

FIG. 7 shows the sequence of about 863 nucleotides of the 5' proximal upstream region of the zebrafish L-FABP coding sequences. Boxes indicate conserved motifs, such as Cdx-2 boxes and CCAAT-boxes. Also shown in this figure are sequences from the coding region, indicated by shading.

FIG. 8A shows the constructs diagrammatically, and indicates the degree of GFP intensity of expression in liver vs. in other organs for each of these constructs. FIGS. 8B-8G show fluorescence micrographs showing GFP expression at different times following microinjection of the noted constructs.

FIG. 9A shows the constructs diagrammatically, and indicates the degree of GFP intensity of expression in liver vs. in other organs for each of these constructs in transient assays. FIGS. 9B-9E show fluorescence micrographs showing GFP expression at different times following microinjection of the noted constructs.

FIG. 10A shows that expression of the indicated construct was still detectable after 6 months of development, and that there were no visible defects in the liver compared with the wild-type liver (FIG. 10B). FIG. 10C shows a transverse cryosection of the liver from a 6-month old transgenic fish.

FIG. 11 shows the sequence of a "liver regulatory element" of the invention. The sequence extends from nt −1944 to nt −1510, which is SEQ ID NO: 1.

FIG. 13A shows sequences of region "A" (shown in red) and region "B" (shown in blue), and indicates the presence of various conserved motifs. FIG. 13B shows, diagrammatically, several constructs in which regions "A" or "B" are deleted, or motifs within region "A" are deleted. The right side of FIG. 13B indicates the degree of GFP intensity of expression in liver vs. in other organs for each of these constructs in transient assays. FIGS. 13C-13J show fluorescence micrographs showing GFP expression at different times following microinjection of the noted constructs.

DETAILED DESCRIPTION OF THE INVENTION

Figure 1:
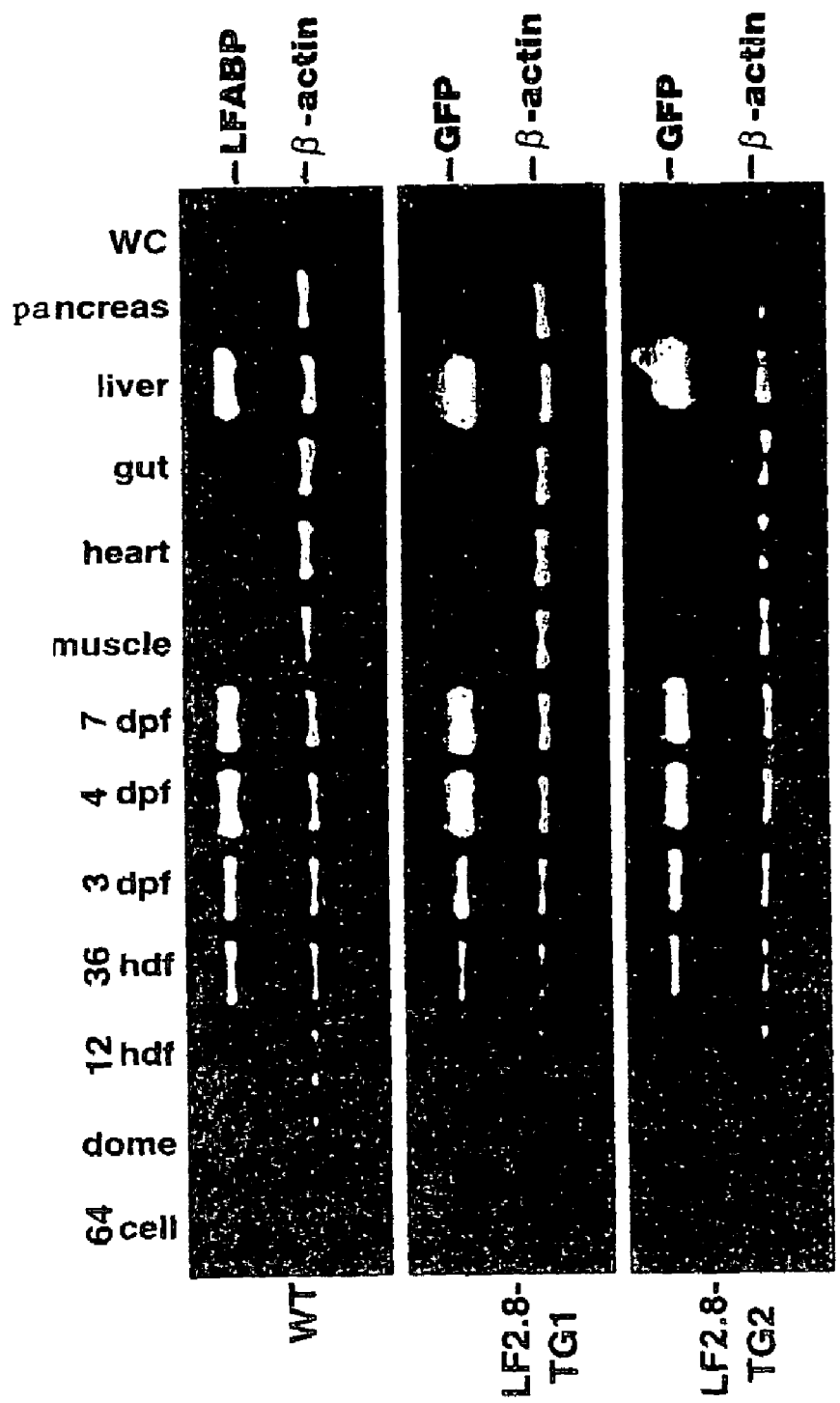
FIG. 1 shows a comparison of the developmental and tissue-specific expression of the endogenous L-FABP gene in wild-type zebrafish and the eGFP transgene in two transgenic lines (LF2.8-TG1 and LF2.8-TG2). RT-PCR was performed to detect message of endogenous L-FABP gene and GFP transgene. PCR products (400 bp for EGFP and L-FABP) from transcripts of EGFP and L-FABP zebrafish gene were detected by RT-PCR at the indicated developmental stages, and in the indicated tissues at 49 dpf. β-Actin (200 bp) was used as a control and was amplified in a same PCR reaction. WC indicates the negative water control. The PCR products were confirmed by sequencing.

The present invention relates to polynucleotide comprising expression control sequences of the invention. As used herein, the term polynucleotide is interchangeable with the terms oligonucleotides, oligomers, and nucleic acids.

The term "expression control sequence" means a polynucleotide sequence that regulates expression of a polypeptide coded for by a polynucleotide to which it is functionally ("operably") linked. Therefore, like the polynucleotide, the expression control sequence can be recombinant polynucleotide, a natural polynucleotide, a synthetic or semi-synthetic polynucleotide, or combinations thereof. The expression control sequence of the invention may be RNA, PNA, LNA, or DNA, or combinations thereof. The preferred control sequence is DNA.

The "expression" of the expression control sequence can be regulated at the level of the mRNA or polypeptide. Thus, the term expression control sequence includes mRNA-related elements and protein-related elements. Such elements include promoters, domains within promoters, upstream elements, enhancers, elements that confer tissue or cell specificity, response elements, ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. An expression control sequence may be linked to another expression control sequence. For example, a tissue-specific expression control sequence, such as the 435 nucleotide sequence of the invention, i.e., the LR sequence, may be linked to a basal promoter element.

The expression control sequences of the present invention include "functional fragments." Such functional fragments retain the ability to exhibit at least some degree of liver-specific, developmentally regulated expression. A skilled worker can readily test whether a sequence of interest exhibits this desired function, by employing well-known assays, such as those described elsewhere herein.

Functional fragments of the invention may be of any size that is compatible with the invention, e.g., of any size that is effective to achieve the desired function (i.e., the ability to direct liver-specific, developmentally regulated expression). For example, the "435 nt" expression control region can be shortened (e.g., by about 20, about 40, or about 60 nucleotides, etc.), provided that the sequence retains the desired function.

The expression control sequences also include "functional variants," which are sequences that exhibit a percent identity to one of the sequences identified above of at least about 70%, preferably at least about 80%, more preferably at least about 90% or 95%, or 98%, provided that the sequence exhibits the desired function noted above.

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=$100[1-(C/R)]$ wherein C is the number of differences between the Reference Sequence and the Compared Sequence over the length of alignment between the Reference Sequence and the Compared Sequence wherein (i) each base in the Reference Sequence that does not have a corresponding aligned base in the Compared Sequence and (ii) each gap in the Reference Sequence and (iii) each aligned base in the Reference Sequence that is different from an aligned base in the Compared Sequence, constitutes a difference; and R is the number of bases in the Reference Sequence over the length of the alignment with the Compared Sequence with any gap created in the Reference Sequence also being counted as a base.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity.

In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

A preferred, non-limiting example of such a mathematical algorithm is described in Karlin et al. (1993) Proc. Natl. Acad. Sci. USA 90:5873-5877. Such an algorithm is incorporated into the NBLAST and XBLAST programs (version 2.0) as described in Altschul et al. (1997) Nucleic Acids Res. 25:3389-3402. When utilizing BLAST and Gapped BLAST programs, the default parameters of the respective programs (e.g., NBLASST) can be used. In one embodiment, parameters for sequence comparison can be set at score=100, wordlength–12, or can be varied (e.g., W=5 or W=20).

In a preferred embodiment, the percent identity between two nucleotide sequences is determined using the GAP program I the GCG software package (Devereux et al. (1984) Nucleic Acids Res. 12 (1):387) using a NWSgapdna. CMP matrix and a gap weight of 40, 50, 60, 70, or 80 and a length weight of 1, 2, 3, 4, 5 or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. Additional algorithms for sequence analysis are known in the art and include ADVANCE and ADAM as described in Torellis et al. (1994) Comput. Appl. Biosci. 10:3-5; and FASTA described in Pearson et al. (1988) PNAS 85:2444-8.

Functional variants of the present invention may take a variety of forms, including, e.g., naturally or non-naturally occurring polymorphisms, including single nucleotide polymorphisms (SNPs), allelic variants, and mutants. They may comprise, e.g., one or more additions, insertions, deletions, substitutions, transitions, transversions, inversions, chromosomal translocations, variants resulting from alternative splicing events, or the like, or any combinations thereof.

Other types of functional variants will be evident to one of skill in the art. For example, the nucleotides of a polynucleotide can be joined via various known linkages, e.g., ester, sulfamate, sulfamide, phosphorothioate, phosphoramidate, methylphosphonate, carbamate, etc., depending on the desired purpose, e.g., improved in vivo stability, etc. See, e.g., U.S. Pat. No. 5,378,825. Any desired nucleotide or nucleotide analog can be incorporated, e.g., 6-mercaptoguanine, 8-oxoguanine, etc.

The phrase "an isolated polynucleotide comprising an expression control sequence that comprises a nucleic acid sequence of SEQ ID NO" refers to an isolated nucleic acid molecule from which that sequence was obtained. Because of sequencing errors, typographical errors, etc., the actual naturally-occurring sequence (e.g., the zebrafish sequence) may differ from a SEQ ID listed herein. Thus, the phrase indicates the specific molecule from which the sequence was derived, rather than a molecule having that exact recited nucleotide sequence, analogously to how a culture depository number refers to a specific cloned fragment in a cryotube.

The "recombinant construct" referred herein contains an expression control sequence of the present invention, which is operably linked to a reporter sequence. That means that a polynucleotide comprising an expression control sequence of interest is cloned in a recombinant construct, such that the expression control sequence is operably linked to a reporter sequence. Preferably, the reporter is a heterologous sequence. However, in cases in which a construct of the invention is introduced into an organism other than zebrafish (e.g., into another type of fish or vertebrates), the naturally occurring (homologous) L-FABP gene may be used as a reporter.

The methods for making the recombinant constructs are conventional. Such methods, as well as many of the other molecular biological methods used in conjunction with the present invention, are discussed, e.g., in Sambrook, et al. (1989), *Molecular Cloning, a Laboratory Manual*, Cold Harbor Laboratory Press, Cold Spring Harbor, N.Y.; Ausubel et al. (1995). *Current Protocols in Molecular Biology*, N.Y., John Wiley & Sons; Davis et al. (1986), *Basic Methods in Molecular Biology*, Elseveir Sciences Publishing, Inc., New York; Hames et al. (1985), *Nucleic Acid Hybridization*, IL Press; Dracopoli et al. *Current Protocols in Human Genetics*, John Wiley & Sons, Inc.; and Coligan et al. *Current Protocols in Protein Science*, John Wiley & Sons, Inc.

Suitable reporter sequences will be evident to those of skill in the art. The reporter sequence can be a polynucleotide, which is detected by, e.g., specific hybridization procedures. These procedures are conventional and well known to the skilled worker. Alternatively, and preferably, the reporter sequence encodes a protein whose presence and/or activity is detected (e.g., measured or, in some cases, quantitated). The amount and/or activity of the reporter protein serves as an indirect measure of gene expression regulated by the expression control sequence (e.g, mRNA initiating at a promoter sequence, or protein translated from the mRNA into protein). Any of a variety of conventional reporter proteins can be employed, including, e.g., green fluorescent protein (GFP), luciferase, β-galactosidase, alkaline phosphatase, chloramphenicol acetyltransferase (CAT), or the like. Other well-known fluorescent reporters, which fluoresce blue, red, etc., or which exhibit greater fluorescence than wild type GFP, can also be used. In a preferred embodiment, the reporter protein is GFP. The use of the reporter protein, GFP, is illustrated in Examples I and II, infra.

Techniques to detect protein reporters, either directly (e.g., by measuring the amount of reporter mRNA) or indirectly (e.g. by measuring the amount and/or activity of the reporter protein) are conventional. Many of these methodologies and analytical techniques can be found in such references as Current Protocols in Molecular Biology, F. M. Ausubel et al., eds., (a joint venture between Greene Publishing Associates, Inc. and John Wiley & Sons, Inc.), Enzyme Immunoassay, Maggio, ed. (CRC Press, Boca Raton, 1980); Laboratory Techniques in Biochemistry and Molecular Biology, T. S. Work and E. Work, eds. (Elseveir Science Publishers B. V., Amsterdam, 1985); Principles and Practice of Immunoassays, Price and Newman, eds. (Stockton Press, NY, 1991); and the like.

For example, changes in nucleic acid expression can be determined by polymerase chain reaction (PCR), ligase chain reaction (LCR), Qβ-replicase amplification, nucleic acid sequence based amplification (NASBA), and other transcription-mediated amplification techniques; differential display protocols; analysis of northern blots, enzyme linked assays, micro-arrays and the like. Examples of these techniques can be found in, for example, *PCR Protocols A Guide to Methods and Applications* (Innis et al., eds, Academic Press Inc. San Diego, Calif. (1990)).

In a preferred embodiment, the amount and/or activity of a reporter expression product (e.g., a protein) is measured. A fluorescent marker, such as GFP, can be detected by detecting its fluorescence in the cell (e.g., in a zebrafish embryo). For example, fluorescence can be observed under a fluorescence microscope. Reporters such as GFP, which are directly detectable without requiring the addition of exogenous factors, are preferred for detecting or assessing gene expression during zebrafish embryonic development. A transgenic zebrafish embryo carrying a recombinant construct of the invention encoding a GFP reporter can provide a rapid real time in vivo system for analyzing spatial and temporal expression patterns of developmentally regulated liver genes.

The recombinant construct of the invention can be cloned into a suitable vector. The vector can then be used, e.g., to propagate the recombinant construct. Generally, before introducing a recombinant construct of the invention into a zebrafish embryo, it is desirable to remove the vector sequences. Preferably, the vector/construct is designed so that the recombinant construct can be excised with one or two appropriate restriction enzyme(s). See, e.g., Example IA4.

Large numbers of suitable vectors are known to those of skill in the art, and many are commercially available. The following vectors are provided by way of example; Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as it is replicable and viable in the host.

As noted above, the invention provides a method for detecting L-FABP promoter activity in a eukaryotic cell by introducing the recombinant construct into the eukaryotic cell, and detecting the presence and/or activity of the reporter sequence in the cell. A variety of eukaryotic cells can be used; suitable cells will be evident to the skilled worker. In preferred embodiments, the reporter sequence encodes GFP, and the eukaryotic cell is in or from a fish, such as zebrafish, or is in or from a zebrafish embryo.

Many art-recognized methods are available for introducing polynucleotides, such as the constructs of the invention, into cells. The conventional methods that can be employed, include, e.g., transfection (e.g., mediated by DEAB-Dextran or calcium phosphate precipitation), infection via a viral vector (e.g., retrovirus, adenovirus, adeno-associated virus, lentivirus, pseudotyped retrovirus or poxvirus vectors), injection, such as microinjection, electroporation, sonoporation, a gene gun, liposome delivery (e.g., LIPOFECTIN® (a cation liposome containing N-[1-(2,3-dioleyloxy)propy]-N,N,N-trimethylammonium chloride (DOTMA)), LIPOFECTAMINE® (a 3:1 (w/w) liposome formulation of the polycationic lipid 2.3-dioleyloxy-N-[2(sperminecarboxamido)ethyl]-N,N-dimethyl-1-propanaminium trifluoroacetate (DOSPA)) (GIBCO-BRL, Inc., Gaithersburg, Md.), SUPERFECT® (polyamidoamino dendrimers) (Qiagen, Inc. Hilden, Germany) and TRANSFECTAM® (dioctadecylamidoglycylspermine) (Promega Biotec, Inc., Madison, Wis.), or other liposomes developed according to procedures standard in the art), or receptor-mediated uptake and other endocytosis mechanisms.

Methods for introducing the recombinant construct into a fish embryo are discussed in more detail elsewhere herein.

As used herein, "transgenic fish" refers to fish, or progeny of a fish, into which an exogenous recombinant construct has been introduced. A fish into which a construct has been introduced includes fish that have developed from embryonic cells into which the construct has been introduced. As used herein, an exogenous construct is a nucleic acid that is artificially introduced, or was originally artificially introduced, into an animal. The term artificial introduction is intended to exclude introduction of a construct through normal reproduction or genetic crosses. That is, the original introduction of a gene or trait into a line or strain of animal by cross breeding is intended to be excluded.

However, fish produced by transfer, through normal breeding, of an exogenous construct (that is, a construct that was originally artificially introduced) from a fish containing the construct are considered to contain an exogenous construct. Such fish are progeny of fish into which the exogenous construct has been introduced. As used herein, progeny of a fish are any fish which are descended from the fish by sexual reproduction or cloning, and from which genetic material has been inherited. In this context, cloning refers to production of a genetically identical fish from DNA, a cell, or cells of the fish. The fish from which another fish is descended is referred to as a progenitor fish. As used herein, development of a fish from a cell or cells (embryonic cells, for example), or development of a cell or cells into a fish, refers to the developmental process by which fertilized egg cells or embryonic cells (and their progeny) grow, divide, and differentiate to form an adult fish.

A transgenic fish of the present invention is one whose somatic and germ cells contain at least one genomically integrated copy of a recombinant construct of the invention. The invention further provides a transgenic fish gamete, including an transgenic fish egg or sperm cell, a transgenic fish embryo, and any other type of transgenic fish cell or cluster of cells, whether haploid, diploid, triploid or other zygosity having at least one genomically integrated copy of a recombinant construct of the invention.

As used herein, the term "embryo" includes a single cell fertilized egg (i.e., a zygote) stage of the organism. Preferably, the recombinant construct is integrated into the fish's somatic and germ cells such that it is stable and inheritable (is stably transmitted through the germ line). The transgenic fish or fish cell preferably contains a multiplicity of genomically integrated copies of the construct; more preferably, the multiple copies of the construct are integrated into the host organism's genome in a contiguous, head-to-tail orientation.

Progeny of the transgenic fish containing at least one genomically integrated copy of the construct, and transgenic fish derived from a transgenic fish egg, sperm, embryo or other fish cell of the invention, are also included in the invention. A fish is "derived from" a transgenic fish egg, sperm cell, embryo or other cell if the transgenic fish egg, sperm cell, embryo or other cell contributes DNA to the fish's genomic DNA. For example, a transgenic embryo of the invention can develop into a transgenic fish of the invention; a transgenic egg of the invention can be fertilized to create a transgenic embryo of the invention that develops into a transgenic fish of the invention; a transgenic sperm cell of the invention can be used to fertilize an egg to create a transgenic embryo of the invention that develops into a transgenic fish of the invention; and a transgenic cell of the invention can be used to clone a transgenic fish of the invention. In some embodiments of the invention, the transgenic fish is sterile. The present invention further includes a cell line derived from a transgenic fish embryo or other transgenic fish cell of the invention, which contains at least one copy of a recombinant construct of the invention. Methods of isolating such cells and propagating them are conventional.

Methods of producing transgenic animals are well within the skill of those in the art, and include, e.g., homologous recombination, mutagenesis (e.g., ENU, Rathkolb et al., *Exp. Physiol.*, 85(6):635-644, 2000), and the tetracycline-regulated gene expression system (e.g., U.S. Pat. No. 6,242,667). See also methods for generating transgenic zebrafish described in U.S. Pat. No. 6,489,458.

The disclosed transgenic fish are produced by introducing a recombinant construct of the invention into cells of a fish, preferably embryonic cells, and most preferably in a single cell embryo. Where the transgene construct is introduced into embryonic cells, the transgenic fish is obtained by allowing the embryo to develop into a fish. Introduction of constructs into embryonic cells of fish, and subsequent development of the fish, are simplified by the fact that embryos develop outside of the parent fish.

The disclosed recombinant constructs can be introduced into embryonic fish cells using any suitable technique. Many techniques for such introduction of exogenous genetic material have been demonstrated in fish and other animals. These include microinjection (described by, for example, Culp et al. (1991) *Proc Natl Acad Sci USA* 88, 7953-7957), electroporation (described by, for example, Inoue et al.(1990), *Cell. Differ. Develop.* 29, 123-128; Muller et al. (1993), *FEBS Lett.* 324, 27-32; Murakami et al. (1994), *J. Biotechnol.* 34, 35-42; Muller et al. (1992), *Mol. Mar. Biol. Biotechnol.* 1, 276-281; and Symonds et al.(1994), *Aquaculture* 119, 313-327), particle gun bombardment (Zelenin et al. (1991), *FEBS Lett.* 287, 118-120), retroviral vectors (Lu et al (1997). *Mol Mar Biol Biotechnol* 6, 289-95), and the use of liposomes (Szelei et al. (1994), *Transgenic Res.* 3,116-119). Microinjection is preferred. The preferred method for introduction of transgene constructs into zebrafish embryonic cells by microinjection is described in the examples.

Embryos or embryonic cells can generally be obtained by collecting eggs immediately after they are laid. It is generally preferred that the eggs be fertilized prior to or at the time of collection. This is preferably accomplished by placing a male and female fish together in a tank that allows egg collection under conditions that stimulate mating. After collecting eggs, it is preferred that the embryo be exposed for introduction of genetic material by removing the chorion. This can be done manually or, preferably, by using a protease such as pronase. A fertilized egg cell prior to the first cell division is considered a one cell embryo, and the fertilized egg cell is thus considered an embryonic cell.

After introduction of the transgene construct the embryo is allowed to develop into a fish. This generally need involve no more than incubating the embryos under the same conditions used for incubation of eggs. However, the embryonic cells can also be incubated briefly in an isotonic buffer. If appropriate, expression of an introduced transgene construct can be observed during development of the embryo.

Fish harboring a transgene can be identified by any suitable means. For example, the genome of potential transgenic fish can be probed for the presence of construct sequences. To identify transgenic fish actually expressing the transgene, the presence of an expression product can be assayed. Several techniques for such identification are known and used for transgenic animals and most can be applied to transgenic fish. Probing of potential or actual transgenic fish for nucleic acid sequences present in or characteristic of a transgene construct is preferably accomplished by Southern or Northern blotting. Also preferred is detection using polymerase chain reaction (PCR) or other sequence-specific nucleic acid amplification techniques. The Examples describe techniques for identifying transgenic zebrafish whose cells express GFP, by assaying for the presence of fluorescence in the embryos.

After "founder" transgenic zebrafish are identified, one can mate them to wild type fish to identify those fish which comprise the transgene in their germ cells, e.g., as described in Example IC. Transgenic zebrafish of the invention can be either male or female. A transgenic zebrafish of the invention can be hemizygous for the transgene, which is the preferred state for maintenance of zebrafish lines. Alternatively, hemizygous zebrafish can be crossed with each other to produce homozygous fish or fish lines. Homozygous diploids can also be produced by other methods, e.g., interruption of the second meiotic divisions with hydrostatic pressure using a French press.

The disclosed recombinant constructs are preferably integrated into the genome of the fish. However, the disclosed transgene construct can also be constructed as an artificial chromosome. Such artificial chromosomes containing more that 200 kb have been used in several organisms. Artificial chromosomes can be used to introduce very large transgene constructs into fish. This technology is useful since it can allow faithful recapitulation of the expression pattern of genes that have regulatory elements that lie many kilobases from coding sequences.

In another embodiment, the invention includes a genomically identical population of transgenic fish, each of whose somatic and germ cells contain at least one genomically integrated copy of a recombinant construct of the invention. The genomically identical population is a unisex population and can be male or female. Preferred embodiments of the genomically identical transgenic fish population are essentially as described for the transgenic fish of the invention. In an alternative embodiment, the invention includes a population of transgenic fish, i.e., an in-bred line, the members of which are not necessarily genomically identical but are homozygous with respect to genomically integrated constructs.

The present invention identifies expression control sequences situated upstream of a vertebrate liver fatty acid binding protein (L-FABP) that, when operably linked to a reporter sequence (e.g., a heterologous reporter), which modulate liver-specific expression of the reporter in embryonic, juvenile, and adult vertebrate, such as a fish. In examples shown herein, the reporter is a nucleic acid sequence that encodes a green fluorescent protein (GFP).

By "modulate" is meant, e.g., to stimulate, enhance, restore, stabilize, increase, facilitate, up-regulate, activate, amplify, augment, induce, or to inhibit, block, destabilize, decrease, down-regulate, diminish, lessen, reduce, etc. synthesis and/or activity of the gene or gene product.

By "liver-specific" is meant a gene that is expressed primarily (or, in some cases, exclusively) in the liver. Such a gene can be a gene involved in the morphogenesis of liver in the organism, although not all genes that are "liver-specific" participate in a morphogenesis pathway.

Specifically, the present invention describes transgenic zebrafish embryos and transgenic zebrafish whose cells comprise at least one genomically integrated copy of the recombinant construct as described above that comprises such an expression control sequence, which is operably linked to a reporter. The pattern of transgene expression in the transgenic organisms recapitulates that of the intact donor zebrafish L-FABP. That is, the expression control sequences reliably drive reporter gene expression in a substantially identical manner to the endogenous L-FABP gene during development of a zebrafish.

The embryonic and adult zebrafish of the invention represent important tools for the understanding of regulatory networks responsible for L-FABP expression in liver. For example, the transgenic organisms can serve as excellent model systems for rapid and efficient in vivo screens of new genes and/or regulatory elements involved in zebrafish liver morphogenesis (development), or for the direct identification of liver mutants in expression-based mutagenesis screens in which disruptions of GFP expression patterns can be observed in embryos. They can also be used for the study of processes involved in liver development, the relationship of cell lineages, the assessment of the effect of specific genes and compounds on the development or maintenance of liver or hepatic cell lineages, and the maintenance of lines of fish bearing mutant genes from liver morphogenesis pathways. Zebrafish of the invention can also serve as a convenient source of labeled (e.g., GFP-labeled) liver cells for in vitro functional analysis.

Advantages of using the zebrafish model, e.g., for studying liver development or for screening for potential modulatory agents, include, i.a., (1) zebrafish organogenesis takes only a few days to produce functional organs (in contrast, mammalian, such as rats or mice, liver development is a cumulative effect of dynamic events which take considerably longer time to develop); (2) zebrafish embryos are external and optically clear, which allows visual analysis of the development of internal structures and cells in living animals; (3) a transgenic zebrafish embryo carrying a recombinant construct of the invention encoding a GFP reporter can provide a rapid real time in vivo system for analyzing spatial and temporal expression patterns of developmentally regulated liver genes; and (4) the presence of a reporter, such as GFP, in a transgenic zebrafish does not elicit toxic reactions in the fish.

The transgenic zebrafish can be used as a model for identifying a drug or an agent that may have effects on liver development. For example, an agent which potentially may affect the liver development (either by enhancing or suppression the function of the liver) can be microinjected to a transgenic zebrafish embryo that contains a gene encoding the GFP. Due to the unique optically clear appearance of the zebrafish embryo and the benefit of green fluorescence derived from the GFP in the transgenic zebrafish, the embryonic liver development can be visually monitored or viewed under a fluorescent microscope. After the visual or microscopic monitor of the progress or regress of liver development, the liver cells can be further isolated from the transgenic fish for in vitro analysis.

Drugs or agents identified in this manner can be used as therapeutic agents for the treatment of conditions related to liver morphogenesis. For example, the agent may be a therapeutic agent for a disease or condition. Alternatively, the agent may be a mutagen, an environmental pollutant, or a small molecule.

By "mutagens" is meant any pollutants, chemical compounds, radioisotopic emissions, and/or electromagnetic radiation that have the potential of causing gene mutations.

By "small molecule" is meant a "compound" that is isolated from natural sources or developed synthetically, e.g., by combinatorial chemistry. In general, such molecule may be identified from large libraries of natural products or synthetic (or semi-synthetic) extracts or chemical libraries according to methods known in the art. Those skilled in the field of drug discovery and development, for example, will understand that the precise source of test extracts or compounds is not critical to the methods of the invention. Accordingly, virtually any number of chemical extracts or compounds can be used in the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon Associates (Merrimack, N.H.) and Aldrich Chemical (Milwaukee, Wis.).

Alternatively, libraries of natural compounds in the form of bacterial, fingal, plant, and animal extracts are commercially available from a number of sources, e.g., Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

The transgenic zebrafish can also be used for screening a gene whose inactivation may interrupt liver development. For example, if the expression of a liver-specific gene is suspected to play a role in liver development, a drug or agent that is known to inhibit the expression of this gene can be microinjected into the embryo of the transgenic zebrafish that contains a reporter gene encoding the GFP. By visually or microscopically monitoring the development of liver, one would gain knowledge regarding the effect of expression of such gene on liver development.

An example for the inhibitor for a specific gene is an antisense oligonucleotide. An antisense oligonucleotides can control gene expression through binding to a DNA or RNA. The antisense oligonucleotide can hybridize to the mRNA and block translation of the mRNA molecule into a polypeptide (see e.g., Okano, J. (1991), *Neurochem.* 56, 560; Oligodeoxynucleotides as Antisense Inhibitors of Gene Expression, CRC Press, Boca Raton, Fla. (1988)).

An antisense oligonucleotide can be made by using the 5' coding portion of a polynucleotide sequence which encodes for a mature polypeptide of the present invention as template. Alternatively, an antisense oligonucleotide can be designed to be complementary to a region of the gene involved in transcription (see, e.g., Lee et al.(1979), *Nucl. Acids Res* 6, 3073; Cooney et al (1988), *Science* 241, 456; and Dervan et al. (1991), *Science* 251, 1360), thereby preventing transcription and the production of encoded polypeptides.

As described in Example 1E, infra, by using a morpholino antisense oligonucleotide, two genes that were putatively involved in liver development in zebrafish—Hex and Xbp-1—were shown, in fact, to be involved in such liver development. Theoretically, any zebrafish gene that lies upstream of L-FABP in the liver morphogenic pathway can be shown to be involved in zebrafish liver development, using such a test. Putative genes can be characterized rapidly and efficiently by the method. Among the genes known to be involved in liver metabolism in other organisms, which could be tested by methods of the invention, are, e.g., HNF1α, HNF1β, HNF3α, HNF3β, HNF4α, Xbp-1, SEK-1, hhex, proxl, Sox17α, albumin, AMBP, endodermin, fibrinogen, transferrin, and transthyretin.

Furthermore, the transgenic fish can further be used for identifying mutants to be used as models for liver diseases and/or liver cancer.

Suitable mutagens to be used in the establishment of mutants in transgenic zebrafish are conventional and well-known in the art. Candidate mutations can be mapped and characterized further to determine in what genes they are located, and how they act, using conventional methods.

Using the mutant transgenic zebrafish as a model, more drug screening and/or biomedical research can be proceeded with particularities and the progression and regression of the diseases or conditions can be visually or microscopically observed.

In a preferred embodiment, the expression control sequence comprises a 435 nucleotide sequence, also known as "LR" (i e., liver-specific regulatory sequence), as shown in FIG. 11 (SEQ ID NO: 1). The LR is shown herein to be important for efficient, liver-specific transcription.

The 435 nucleotide sequence or LR discussed above does not, by itself, direct liver-specific transcription. Rather, it functions in association with a basal promoter (core promoter), e.g., when it is linked to a basal promoter. In the Examples discussed below, the LR acts in conjunction with the zebrafish core promoter (e.g., in the construct comprising the about 2.0 kb sequence of SEQ ID NO:3). Example IID shows that the LR also drives liver-specific expression if it is cloned upstream of the early SV40 basal promoter. The LR functions in a liver-specific manner if associated with any core promoter, many of which will be evident to those of skill in the art. Typical core promoters that are suitable include, e.g., promoters from the viruses CMV (cytomegalovirus) and RSV (Rous sarcoma virus), or the like.

Figure 13:
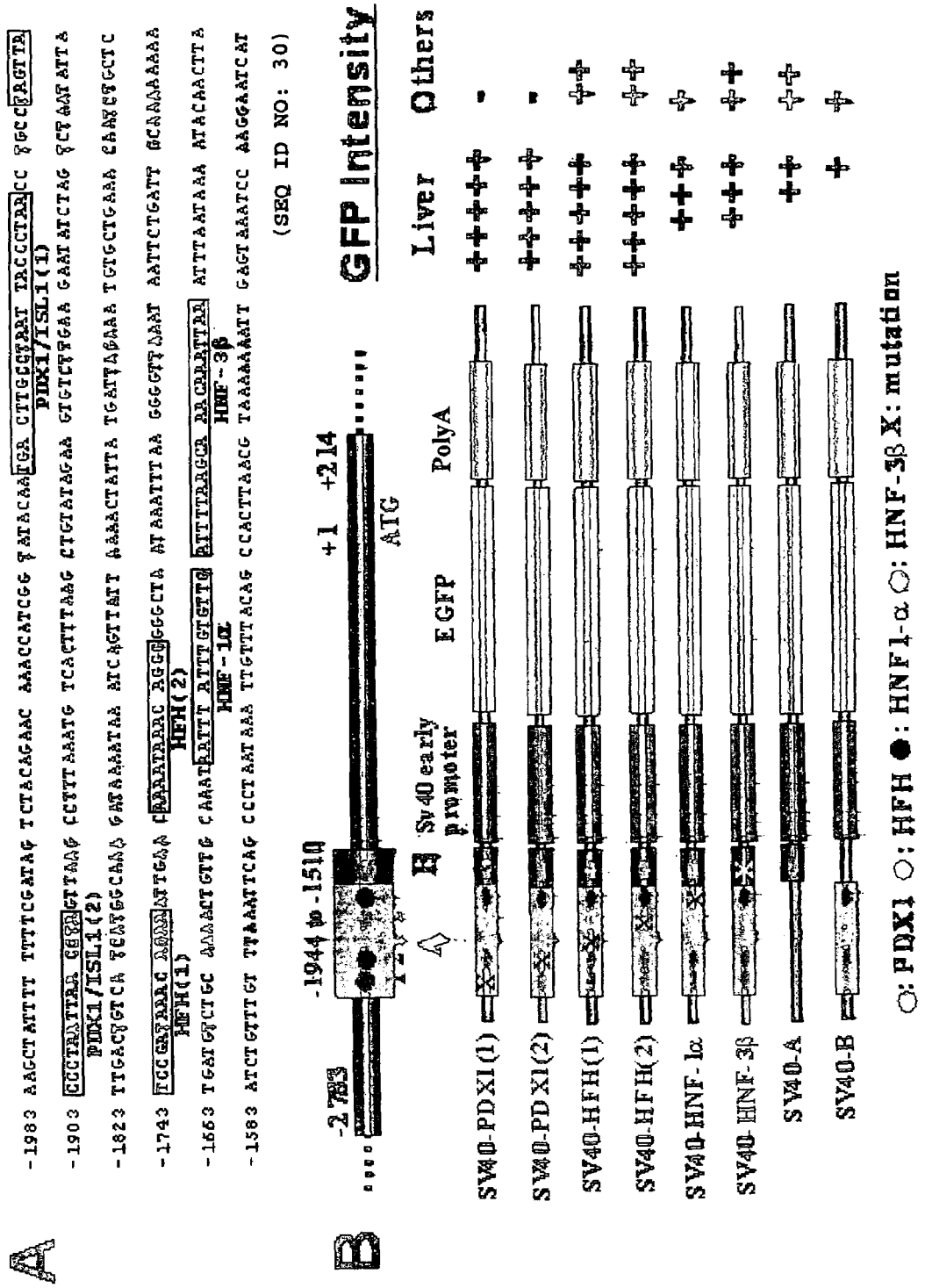
FIG. 13 shows the role of various sequences of the zebrafish L-FABP upstream region.
Figure 13:
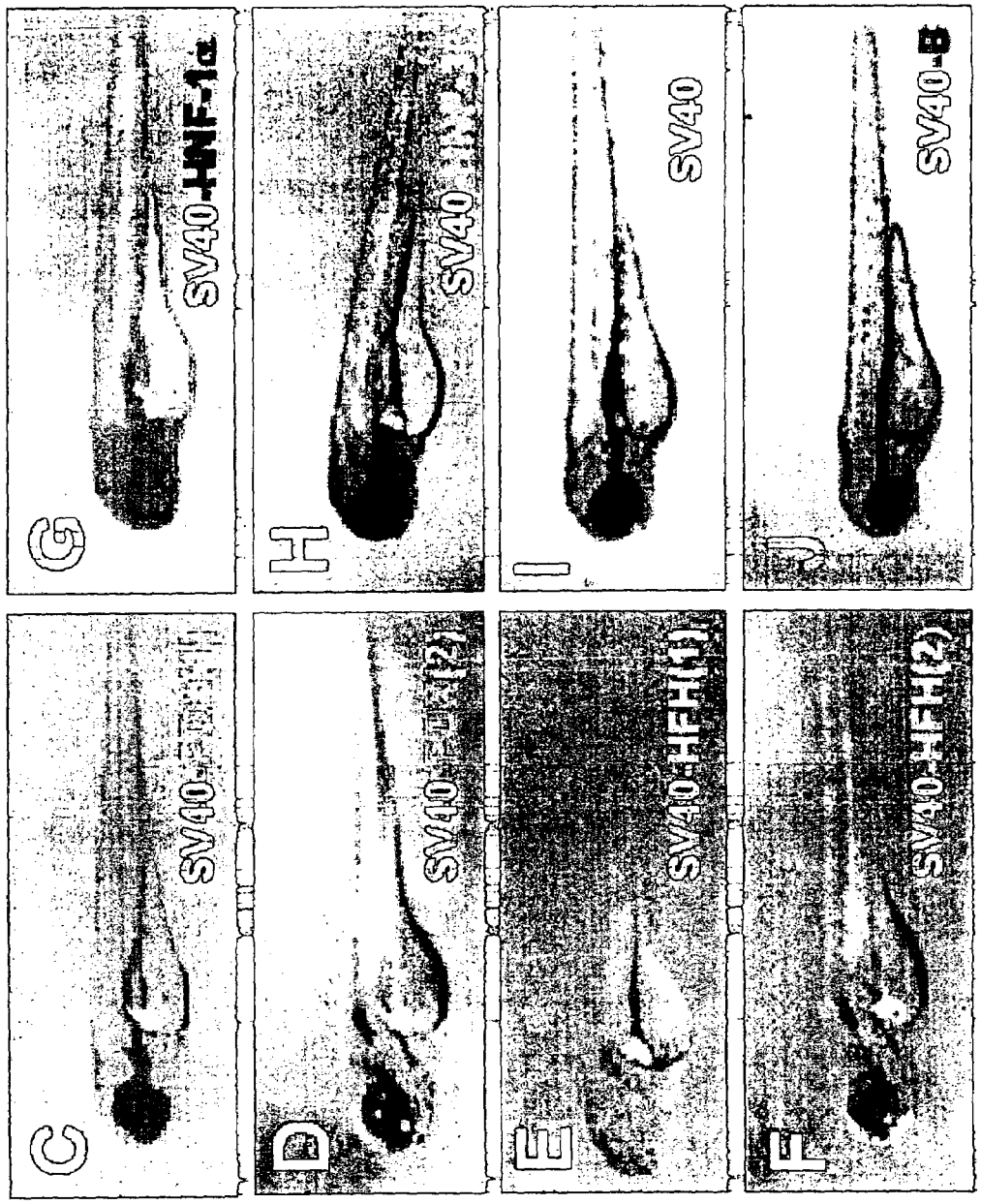

In one embodiment of the invention, the expression control sequence lacks the sequence motifs for PDX1(1) and/or PDX1(2), shown in FIG. 13, which are located within the LR; and/or the expression control sequence lacks the sequence extending from about nt −1944 to about nt −1890 (i.e., a deletion of both the PDX1(l) and PDX1(2) motifs and adjacent sequences). As shown in Example II, the motifs PDX1(1) and PDX1(2) are not required for efficient, liver-specific gene expression.

In another embodiment, an expression control sequence of the invention comprises, in addition to a basal promoter sequence, one or more of the binding sites for HFH(1), HFH (2), HNF-1α and HNF-3β, which are located within the LR, as shown in FIG. 13.

An expression control sequence of the invention may comprise, in addition to the LR, additional zebrafish sequences from the L-FABP upstream region.

In one embodiment, the expression control sequence comprises an about 2.8 kb sequence extending from about nt −2782 of the upstream region to about nucleotide −1 preceding the start of the coding sequence, inclusive. A sequence of 2960 nucleotides including 2783 nucleotides of the region upstream of the L-FABP coding sequence plus some coding sequences of the L-FARB protein is shown in FIG. 6 (SEQ ID NO: 2). This sequence is deposited in GenBank as AF512998. This sequence provides reference points for mapping the position of nucleotides discussed herein, such as nt −2782, and the endpoints of the 435 nt expression control sequence.

In another embodiment, the expression control sequence comprises the sequence extending from about nucleotide −1944 of the upstream region to about the 5' end of the 435 nt sequence. Thus, e.g., an expression control sequence of the invention can comprise an about 2.0 kb sequence extending from about nt −1944 of the upstream region to about nucleotide −1, inclusive. In other embodiments, the expression control sequence comprises a sequence that extends from any nucleotide between about nucleotide −2782 and about nucleotide −1944 of the upstream region to about the 5' end of the 435 nt sequence. The term "zebrafish sequence," as used herein, includes sequences that occur naturally in a zebrafish, including naturally occurring allelic variants.

The following examples are illustrative, but not limiting the scope of the present invention. Reasonable variations, such as those occur to reasonable artisan, can be made herein without departing from the scope of the present invention. Also, in the following examples, all temperatures are set forth in uncorrected degrees Celsius; and, unless otherwise indicated, all parts and percentages are by weight.

The Examples are divided into two. Example I shows that a sequence containing about 2.8 kb nucleotides of the upstream region flanking the zebrafish L-FABP coding sequence harbors all the necessary information for specifically directing expression of a reporter (in the exemplified case, green fluorescent protein (GFP)) in developing zebrafish liver in a manner analogous to the expression of the naturally occurring FABP gene. In brief, Example IB describes transient transgenic analysis, which showed that the GFP expression is highly specific and seen almost exclusively in the liver primordia of embryos injected with the transgene sequence. Example IC describes the production of germline-transmitting transgenic zebrafish that comprise, in their somatic and germ cells, at least one integrated copy of a recombinant construct in which the about 2.8 kb expression control sequence is operably linked to a GFP reporter sequence. Seven F2 lines are described, which exhibit inheritance rates consistent with Mendelian segregation. Example ID illustrates temporal and spatial expression of the construct in zebrafish embryonic stages. Both the construct and endogenous L-FABP mRNAs are first expressed in 36 embryos, and are abundantly expressed in the liver, but are not detected in other organs or tissues.

In further studies, a survey of the upstream region sequences with the Genomatrix MatInspector database identifying a number of putative transcription factor binding sites was conducted. The results suggest that the proximal region upstream of the L-FABP coding sequences contains several consensus motifs, indicating that the core promoter (sometimes referred to herein as a "basal promoter") is located around this region. A proximal upstream region is shown in FIG. 7.

Example II describes serial deletion analysis of the upstream region, and shows that the about 2.0 kb flanking sequence confers correct liver-specific and developmentally regulated expression of GFP in transgenic zebrafish, but that further deletions of the upstream region show progressively reduced amounts of liver-specific expression, and, eventually, no expression at all. Thus, the about 2.0 kb of flanking sequence contains promoter regions and/or regulatory elements necessary to restrict L-FABP gene expression to the liver. This Example further indicates that a 435 nt sequence (extending from nt −1944 to nt −1510, inclusive), i.e., the LR, is important for liver-specific activity and that the about 1.0 kb of 5' sequence flanking the coding sequence contains the core promoter for the zebrafish L-FABP gene.

The following examples are illustrative, but not limiting the scope of the present invention. Reasonable variations, such as those occur to reasonable artisan, can be made herein without departing from the scope of the present invention. Also in describing the invention, specific terminology is employed for the sake of clarity. However, the invention is not intended to be limited to the specific terminology so selected. It is to be understood that each specific element includes all technical equivalents which operate in a similar manner to accomplish a similar purpose.

EXAMPLES

I. In vivo Studies of Liver-Type Fatty Acid Binding Protein (L-FABP) Gene Expression in Liver of Transgenic Zebrafish A. Materials and Methods 1. Fish Maintenance Adult zebrafish were obtained from the local aquarium store and maintained in our own fish facility with a controlled light cycle of 14 h light/10 h dark at 28° C. They spawned soon after the onset of the light period, and the fertilized eggs were collected at the one-cell stage.

2. Inverse Polymerase Chain Reaction (IPCR)

For IPCR amplification, 10 µg of zebrafish genomic DNA was digested with NcoI for 16 h. The digested DNA was phenol/chloroform-extracted, ethanol-precipitated, and then resuspended in 100 µl ligation buffer (50 mM Tris-HCl pH 7.4, 10 mM $MgCl_2$, 10 mM dithiothreitol, 1 mM adenosine triphosphate (ATP)) to reach a final concentration of 50-100 ng/µl. The reaction was initiated by addition of T4 DNA ligase (Promega) to 0.1 units/µl and allowed to proceed for 24 h at 16° C. The circularized DNA was then ethanol-precipitated, dried, and resuspended in 50 µl distilled water. The IPCR reactions were made up with 1 µl of recircularized genomic DNA in a final volume of 50 µl containing 1×Adv PCR buffer (Clontech), 0.2 mM of each dNTP, 0.25 µM of each primer and 0.5 units of Adv DNA polymerase (Clontech). The IPCR primers (LF-1, 5'-CAA AGA TGT GAA GCC AGT GAC AGA-3' (SEQ ID NO: 10); LF-2, 5'-TTT AAT GAC CTC TTC TGG CAG AGA-3') (SEQ ID NO: 11) complementary to a 450-by zebrafish expressed sequence tag (EST) (GenBank accession number AI 545956) were designed in such a way so that their extension results in the synthesized strands polymerized in opposite directions to each other in the initial cycle. As a first step, the samples were denatured at 95° C. for 2 min. This was followed by 35 cycles of 0.5 min denaturation at 95° C., 0.5 min primer annealing at 60° C. and 3 min extension at 68° C., with a final extension at 68° C. for 4 min. The 2.8-kb IPCR product generated from zebrafish genomic DNA was ligated into the pEGFP-Cl vector (Clontech). The resulting plasmid DNA was named pLF2.8-EGFP. The proximal promoter regions were then sequenced for verification based on the 5'-sequences from the L-FABP cDNA sequences.

3. Reverse Transcription (RT)-PCR (IPCR)

For RT-PCR, one-step RT-PCR (Life Technologies) was performed, using total RNA from various developmental stages. β-Actin was used as a control and was amplified in a same PCR reaction tube for detecting L-FABP or GFP transcripts. The primers used were: L-FABP: 5'-GCTCTA GAA TGA AGA GAT ACC AGT GTC TGT TC-3' (forward) (SEQ ID NO:12), 5'-CCG CTC GAG TTT GTC GTG ACC CCG GAT GTG GCT-3' (reverse) (SEQ ID NO:13); β-actin: 5'-GTC CCT GTA CGC CTC TGG TCG-3' (forward) (SEQ ID NO:14), 5'-GCC GGA CTC ATC GTA CTC CTG-3' (reverse) (SEQ ID NO:15). The RT-PCR program was one cycle of 50° C. for 30 min and 94° C. for 2 min, followed by PCR amplification with 35 cycles of 94° C. for 0.5 min, 57° C. for 0.5 min, 72° C. for 0.5 min and a final extension of one cycle at 72° C. for 7 min. The RT-PCR products were subjected to 3% agarose gel electrophoresis. All PCRs were carried out using a Perkin-Elmer/Cetus Thermocycler 9600.

4. Microinjection of Zebrafish Embryos and Production of Transgenic Zebrafish Lines To construct a permanent transgenic line, the vector backbone of pLF2.8-EGFP was removed by digesting with SfiI and NotI. Digested DNA was adjusted to 500 ng/µl in 5 mM Tris, 0.5 mM ethylenediamine tetraacetic acid (EDTA), 100 mM KCl and 0.1% phenol red. For transient expression, an intact circular form of plasmid DNA constructs was adjusted to 100 ng/µl. Approximately 200 pl of DNA solution was injected into the blastomere of early one-cell stage embryos with a glass micropipette. At 36 h postinjection, fish were examined using fluorescence microscopy, and GFP-expressing fish were saved. Germline integrated transgenic zebrafish were selected from these GFP-positive fish by raising them to sexual maturity and breeding them with wild-type fish. Progeny from these fish (at least 100 progeny) were screened for GFP expression and GFP-positive fish were saved for further analysis and breeding.

5. Morpholino Injections

Morpholino antisense oligonucleotides targeted to hhex (zebrafish Hex) (GenBank accession number AF131070) and zXbp-1 (zebrafish Xbp-1) (GenBank accession number AF420255) gene were obtained from Gene Tools (Corvallis, Oreg., USA). hhex MO sequence: 5'-GCG CGT GCG GGT GCT GGA ATT GCA T-3' (SEQ ID NO:16); zXbp-1 MO sequence: 5'-CGG TCC CTG CTG TAA CTA CGA CCA T-3' (SEQ ID NO:17). Control morpholinos of hhex and zXbp-1 were designed to include four base mutations compared to the original MO sequences.

6. Whole-mount In Situ Hybridization

The antisense digoxigenin-labeled RNA probe for the 5'-untranslated region (UTR) of zebrafish L-FABP was produced using a DIG-RNA labeling kit (Roche), following the manufacturer's instructions. In situ hybridizations were carried out on whole-mount embryos as previously described (Westerfield, M. (1993) *The Zebrafish Book. A guide for the laboratory use of zebrafish (Danio rerio)*. University of Oregon Press, Eugene, Oreg.; Jowett, T. (2001) *Methods* 23, 345-358).

7. Tissue Sections

LF2.8-EGFP transgenic fish were perfused with 4% paraformaldehyde, washed with phosphate-buffered saline (PBS), cryoprotected in 30% sucrose, frozen in omithine carbamoyltransferase (OCT) (Miles Inc.) and sectioned at 15 µm on a cryostat.

8. Optics

Whole-mount in situ hybridization patterns were observed with a Zeiss Axioscope microscope. For analyzing GFP fluorescent patterns, embryos and larvae were anesthetized with 0.05% 2-phenoxyethanol (Sigma) and GFP expression was examined under a fluorescein isothiocyanate (FITC) filter on the ECLIPSE E600 microscope (Nikon) equipped with the DXM 1200 CCD camera (Nikon). For fluorescence imaging by confocal laser scanning microscopy (CLSM), we used a Leica TCSNT system fitted to a Leica microscope with a 20× objective (Nikon). Optical sections were scanned at regular increments of 0.5-1 µm. Three-dimensional reconstructions and rotations were computed using TCSNT version 1.6.587 software (Leica).

B. IPCR Cloning and Transient Transgenic Analysis of the L-FABP Gene Promoter

In order to isolate a zebrafish liver-specific promoter region, the IPCR technique was used as described above and a 2.8-kb 5'-flanking region of the L-FABP gene was isolated (Denovan-Wright et al. (2000) *Biochim. Biophys. Acta* 1492, 227-232). The pLF2.8-EGFP expression vector produced by coupling 2783 bp of 5'-flanking region of the L-FABP gene and a partial 5' proximal coding region to an eGFP reporter gene, was examined for its promoter activity after removal of bacterial vector sequences. In a transient transgenic analysis, although the number of fluorescent cells and intensity of fluorescence varied a little among the transient transgenic fish, GFP expression was highly specific and seen almost exclusively in the liver primordia of the embryos injected with the transgene sequence (Table 1).

TABLE 1

Efficiency of transient transgenic GFP expression in the LF2.8EGFP-injected transgenic zebrafish larvae at 3 dpf.

| Experiment | number of embryos injected (one cell stage) | number of surviving embryos (20-30 h) | Green fluorescence patterns in liver (%) | Green fluorescence patterns in other regions (%) |
|---|---|---|---|---|
| 1 | 225 | 212 | 135 (60%) | 4 (1.9%) |
| 2 | 217 | 198 | 111 (51%) | 1 (0.5%) |
| 3 | 209 | 202 | 119 (57%) | 0 (0%) |

DNA concentration of each experiment is 100 µg/ml. 200 nl of the DNA solution was injected for experiment 1, 100 nl for experiment 2, and 50 nl for experiment 3.

In three independent experiments, 50-60% of embryos were observed to have green fluorescent cells in the liver primordia of 3 dpf larvae.

C. Generation of LF2.8-EGFP Transgenic Zebrafish

To confirm the tissue specificity of the L-FABP promoter and to generate stable GFP expression in the zebrafish liver, the LF2.8-EGFP construct was used to produce germline-transmitting transgenic zebrafish lines. Transgenic fish were produced by microinjection of the LF2.8-EGFP construct (after removal of bacterial vector sequences) into one-cell stage zebrafish embryos. The injected embryos were examined at 3-5 dpf by fluorescence microscopy, grouped according to the intensity of fluorescence, raised to sexual maturity, and screened for potential founders. The founder fish were mated to wild-type fish and the fluorescence of their 3-5 day-old progeny was examined using fluorescence microscopy. The embryos injected with the LF2.8-EGFP construct and isolated from seven transgenic founders (three male and four female) in 268 adult fish were raised. Founder fish had highly mosaic germlines, with F1 inheritance rates ranging from 7 to 32%. The 42-51% F2 inheritance rates seen in all the seven lines were consistent with those expected for Mendelian segregation and with rates described in previous reports. The frequency of germline transmission is summarized in Table 2.

TABLE 2

Inheritance of LF2.8-EGFP in transgenic zebrafish lines

| Founders | Sex | F1 | % | F2 | % |
|---|---|---|---|---|---|
| | | | Inheritance of GFP expression | | |
| LF2.8-TG1 | M | 42/201 | 21% | 166/345 | 48% |
| LF2.8-TG2 | M | 15/225 | 7% | 126/279 | 45% |
| LF2.8-TG3 | M | 41/259 | 16% | 111/253 | 44% |
| LF2.8-TG4 | F | 29/266 | 11% | 155/303 | 51% |
| LF2.8-TG5 | F | 61/307 | 20% | 146/298 | 49% |
| LF2.8-TG6 | F | 43/151 | 28% | 132/312 | 42% |
| LF2.8-TG7 | F | 55/171 | 32% | 125/255 | 49% |

The F1 transgenic progeny from each line were derived from single pairs of fish by crossing founder males or females to wild-type females or males. The F2 transgenic progeny from each line were derived from single pairs of fish by crossing F1 transgenic males or females to wild-type females or males.

D. The LF2.8-eGFP Transgenic Expression Mimics Endogenous L-FABP Expression

Liver-specific expression of L-FABP had been shown in adult zebrafish. However, no temporal and spatial expression of L-FABP had been further analyzed in zebrafish embryonic stages. To provide additional evidence that L-FABP-positive cells were expressed in early liver primordia formation, the expression of L-FABP and that of ceruloplasmin (Cp) were compared, which showed expression in zebrafish liver primordia. At 3 dpf, the expression of L-FABP (LF) in embryonic liver primordia was very similar to that of ceruloplasmin (Cp). In order to assess whether the transgene conferred developmental and tissue-specific expression, expression of L-FABP and the eGFP transgene were compared at various developmental stages. Total RNA was individually purified from the various stages of embryos and from tissues of transgenic and wild-type fish. RT-PCR was performed to detect expression of the endogenous L-FABP gene and the GFP transgene. β-Actin message was also amplified as a control for the quality of the RNA. In the developmental process of zebrafish, maternally supplied L-FABP mRNA is not detected from the stages of one cell to early embryonic stage (12 hpf stage) and the L-FABP mRNA is first expressed in the 36 hpf embryos. Zebrafish L-FABP mRNA was abundantly expressed in the liver and was not detected in other organs/tissues including gut, heart, pancreas and muscle (FIG. 1). Thus, the expression pattern of the LF2.8-EGFP transgene was very similar to that of the endogenous L-FABP gene.

Figure 2:
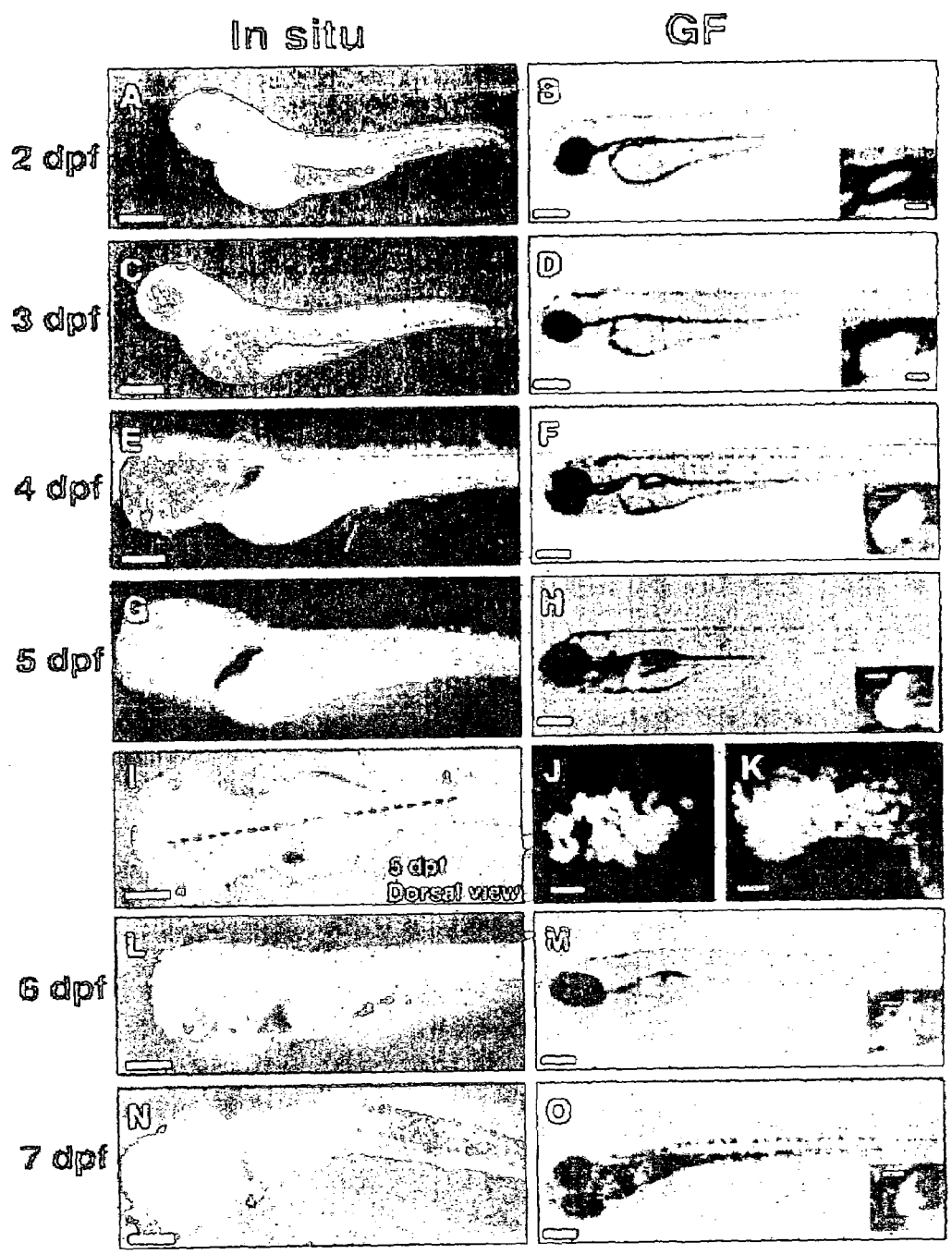
FIG. 2 shows a comparison of the endogenous L-FABP expression in embryonic progeny of wild-type zebrafish with expression of eGFP in progeny of the transgenic line LF2.8-TG1.

To provide additional evidence for the similarity of the expression patterns, a series of in situ hybridizations in one of the LF2.8-EGFP transgenic lines at different developmental stages were performed (FIG. 2). From 12 to 30 hpf, no signals could be detected by either in situ analysis of L-FABP expression in wild-type embryos or by eGFP fluorescence in transgenic embryos. Only a few hundred cells expressing endogenous L-FABP in ventral endoderm near the heart chamber were faintly detected by in situ hybridization in 36 hpf embryos, while transgene expression was easily seen in a group of cells near the same region at the same stage. This difference may be due to the high stability of GFP. The transcripts were detectable around 2 dpf first in the liver primordia (FIG. 2A) and small green fluorescent liver primordia were also seen in the 2 dpf transgenic embryo (FIG. 2B). L-FABP is predominately expressed in functional liver due to its biological functions for lipid metabolism. Zebrafish liver may start its function after the stage of 2 dpf (hatchout). Thus, weak or no GFP fluorescence can be seen in the early stage of transgenic embryos. The liver primordia continued to be restricted to this similar region at 3 dpf (FIGS. 2C, D). The size of the liver primordia was increased in the 4 dpf larvae (FIGS. 2E, F), and further increased in the 5 dpf larvae (FIGS. 2G, H). The 5 dpf larvae showed a similar oval shape structure, but this was much larger than seen in the 3 and 4 dpf liver primordia. At 5 dpf the liver became an asymmetrical organ, and was seen at the left-hand side of the trunk (FIG. 2I).

To estimate the size of embryonic liver, three-dimensional images of liver structure of the 4 dpf and 5.5 dpf larvae were obtained by confocal laser scanning microscopy (CLSM). GFP-expressing cells were organized into an oval-shaped cluster in the 4 dpf larvae (FIG. 2J) and a conical structure in the 5.5 dpf larvae (FIG. 2K). The size of the 4 dpf larval liver as measured by CLSM was about 105 µm in width, 200 µm in length and 20-75 µm in thickness; at 5.5 dpf these values increased to about 91 µm in width, 320 µm in length, and 45-102 µm in thickness. A significant increase in cell number was seen in the 6 dpf liver, and GFP-expressing cells were reorganized into a larger conical structure (FIGS. 2L, M). The liver becomes a crescent-shaped structure at 7 dpf (FIGS. 2N, O). These results suggest that the pattern of transgenic expression is consistent with the expression pattern of the endogenous genes.

Figure 3:
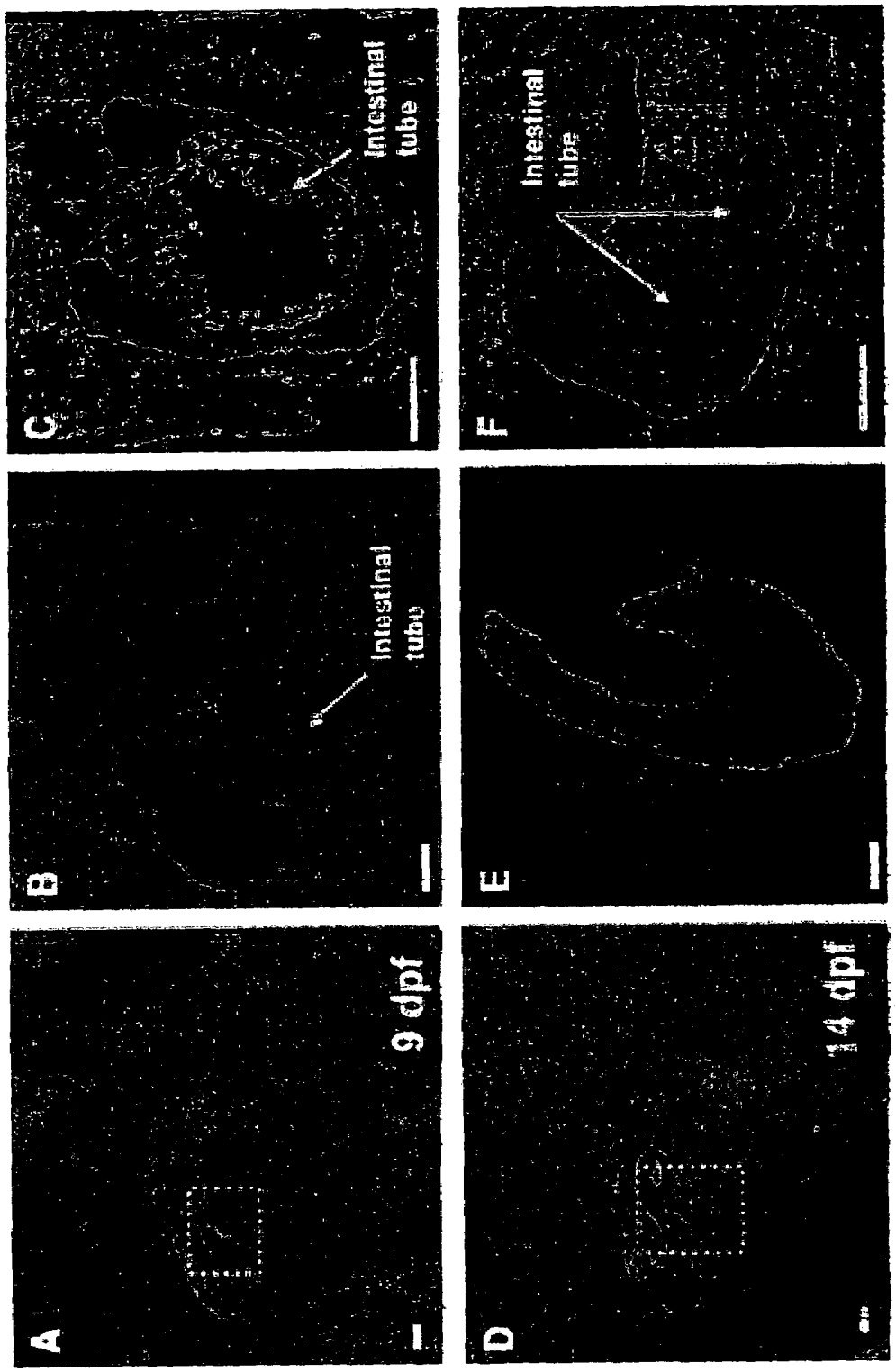
FIG. 3 shows an analysis of GFP expression in the liver of larval transgenic fish.
Figure 4:
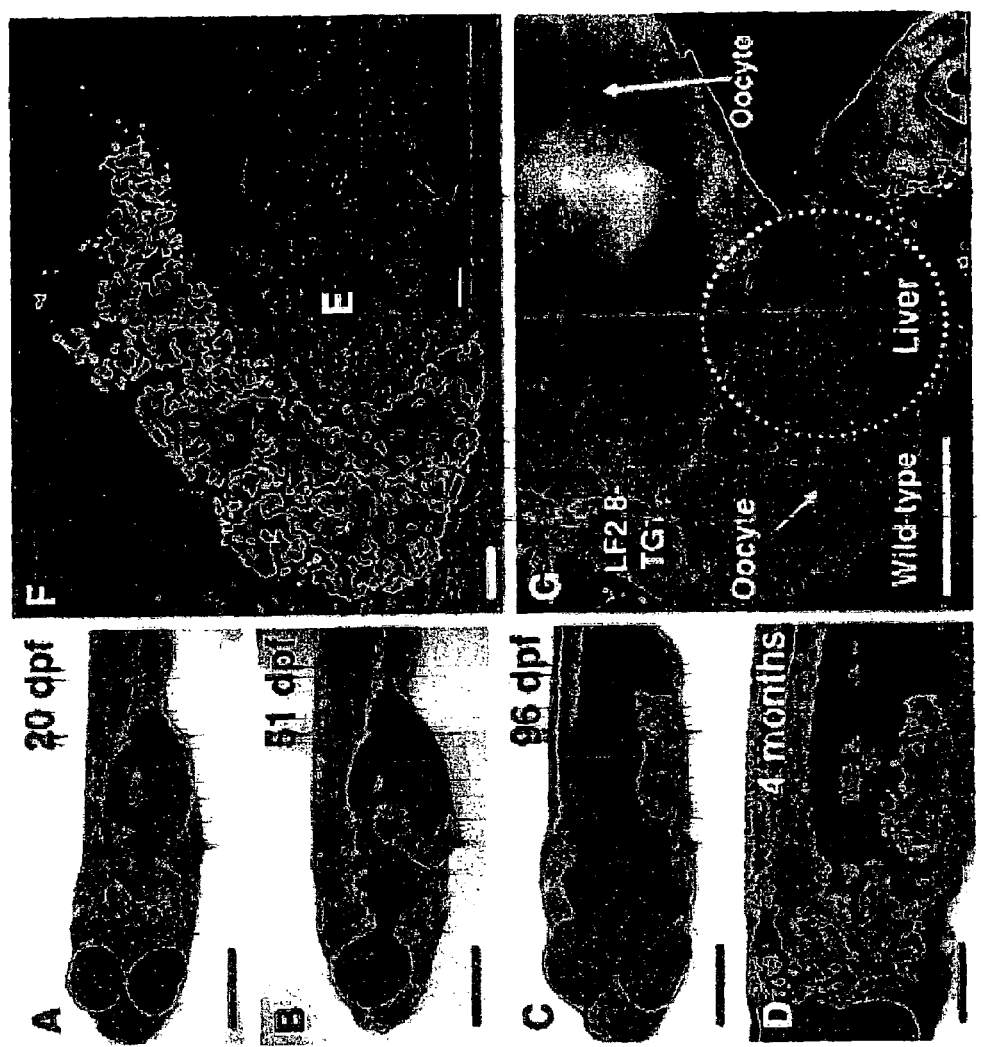
FIG. 4 shows an analysis of GFP expression in the liver of juvenile and adult transgenic fish.

The liver still showed a conical-shaped structure at 9 dpf (FIG. 3A), similar to what was seen at 7 dpf (FIGS. 2N, O). However, the anterior end of the intestinal tube was surrounded by the liver in 9 dpf transgenic embryos (FIGS. 3B, C). The liver became a crescent-shaped structure at 14 dpf (FIGS. 3D, E), and was significantly longer at this time (FIG. 3E, F). For juvenile and adult transgenic fish, GFP expression was strong in juvenile fish at 20 dpf (FIG. 4A) and 51 dpf (FIG. 4B), and in adult fish at 96 dpf (FIG. 4C) and 120 dpf (FIG. 4D). Green fluorescence was only observed in the liver in sagittal sections from 51 dpf transgenic fish (FIG. 4E), and individual GFP-labeled liver cells (hepatocyte) were clearly discerned at higher magnification (FIG. 4F). Surprisingly, GFP fluorescence in liver was still highly detectable and there was no visible defect in the liver after 13 months of development. In fact, seven independent transgenic lines show continual stable transmission and high level of GFP expression in liver and have been maintained for over six generations.

Figure 5:
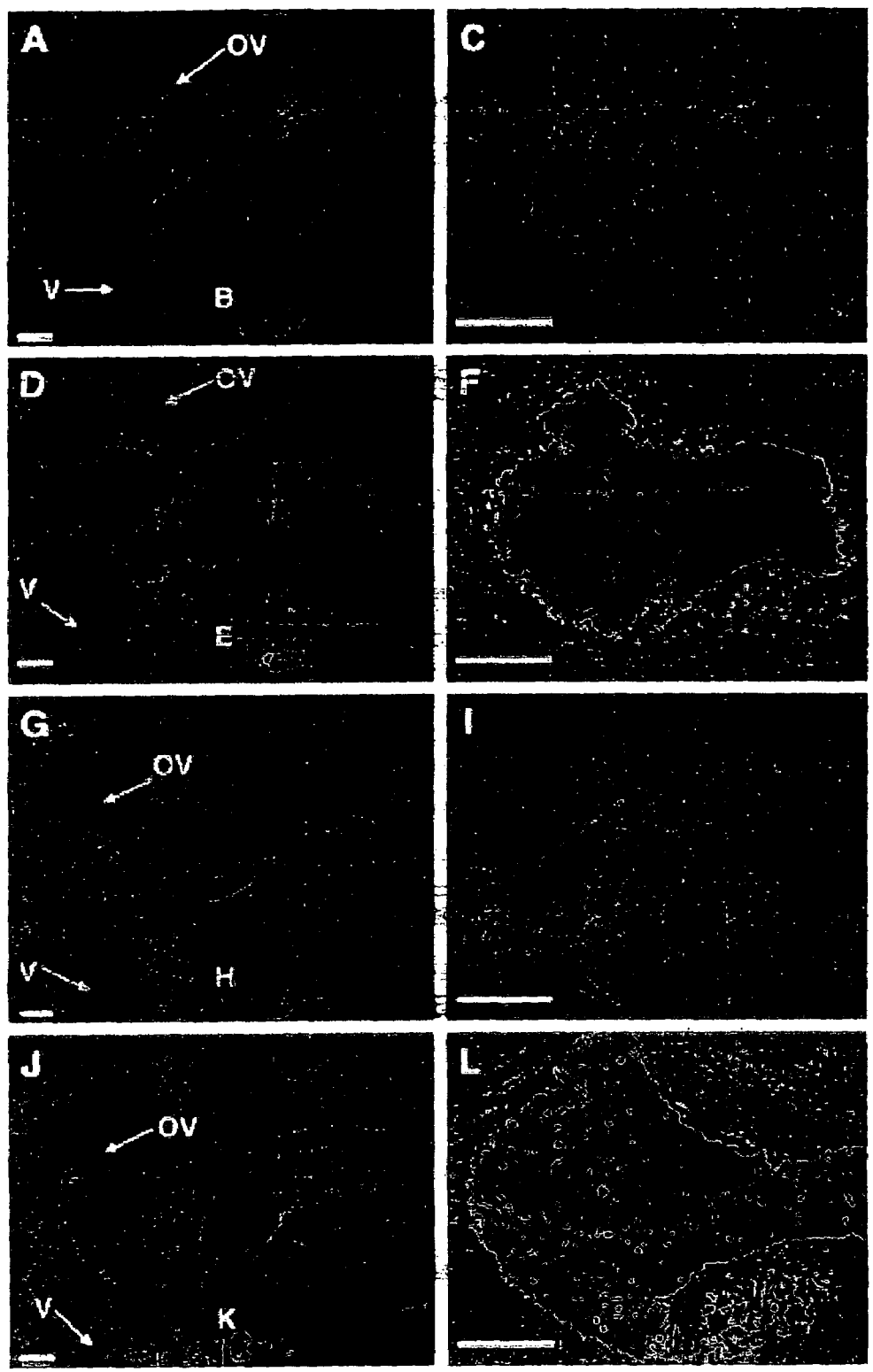
FIG. 5 shows the effect of zebrafish Hex and Xbp-1 morpholinos (hhex-MO and zXbp-1-MO) on zebrafish hepatogenesis. Zebrafish embryos were injected at the one-cell stage with a low concentration (100 ng/μl for hhex-MO; 200 ng/μl for zXbp-1-MO) of the morpholinos complementary to 5'-proximal regions of the cDNA as described above.

E. The LF2.8-EGFP Transgenic Zebrafish Lines Enable Rapid or in vivo Screening for Genes or Mutants in Liver Development Studies In mice, gene inactivation of Hex, Xbp-1, Sekl, c-Jun and N-myc has been shown to result in an interruption of liver development. To demonstrate that LF2.8-EGFP transgenic lines could be used for high throughput analyses of liver mutants, and to compare the activity of these genes involving liver formation, morpholinos (hhex-MO and zXbp-1-MO) targeting zebrafish Hex and Xbp-1 were injected into one-cell stage LF2.8-EGFP transgenic embryos. Embryos injected with low concentration (100 ng/µl) of the hhex-MO solution started to show a reduced liver phenotype with no other defects at 4 dpf (FIGS. 5A, B, C). The liver size of embryos injected with medium concentration (400 ng/µl) of the hhex-MO solution was significantly reduced, and the embryos started to show different trunk defects from 4 to 6 dpf. The liver of embryos injected with high concentration (800 ng/µl) of the hhex-MO solution was barely visible at the stage of 4 dpf, and the embryos start to show severe edema at the stage of 5 dpf. There were no effects on the liver of embryos injected with the hhex control-MO (FIGS. 5D, E, F). In previous studies, zebrafish Hex morphants showed phenotypes including reduced or absent liver, and lack of digestive organ chirality.

It was reported that in mouse Hex mutant embryos, the liver diverticulum could be identified in both Hex$^{+/-}$ and Hex$^{-/-}$ embryos as a small region of cells at embryonic day 9.5 (E9.5). At E13.5, a normal liver was observed in Hex$^{+/+}$ and Hex$^{+/-}$ embryos but this organ was absent in Hex$^{-/-}$ embryos, which also had brain defects. The data of the present invention were thus in agreement with the reported studies, in that initial liver specification was seen to occur in both mouse Hex$^{-/-}$ mutants and zebrafish hex morphants at early stages, but liver organogenesis fails later.

In zebrafish Xbp-1 morphants, a reduced size of liver with a significant decrease in cell population was also seen in embryos injected with low concentration (200 ng/µl) of the zXbp-1-MO at 4 dpf (FIGS. 5G, H, I). The liver size of embryos injected with medium concentration (800 ng/µl) of the zXBp-1-MO solution was similar to that of embryos injected with low concentration (200 ng/µl) of the zXbp-1-MO solution, but the embryos started to show low growth rate (smaller body length) at 5 dpf. The liver of embryos injected with high concentration (1600 ng/µl) of the zXbp-1-MO solution was markedly reduced and the embryos showed severe edema at 4 dpf. There were no effects on the liver of embryos injected with the zXbp-1 control-MO solution (FIGS. 5J, K, L).

Mice lacking Xbp-I displayed hypoplastic fetal livers and hepatocyte development itself was severely impaired by diminished growth rate. The data of the present invention agreed in that the delayed hepatocyte growth seen in mouse Xbp-I-/- mutants was similar to the reduced liver cell population observed in zebrafish xbp-I morphants at early stages, followed by impaired liver organogenesis at the later stages.

As shown in Table 3, injection of hhex-MO and zXbp-1-MO resulted in dose-dependent reduction of GFP expression in the 4 dpf LF2.8-EGFP transgenic embryos due to an interruption of liver development. The embryos injected with high concentration of the hhex-MO and zXbp-1-MO solution displayed other embryonic abnormalities, which might be due to a significant loss of liver function later. The small livers present in the embryos injected with low concentration of the morpholinos did not arise from a non-specific developmental delay (FIGS. 5D, E, J, K). Thus, the dramatic effects of size reduction and altered shape on the morphant livers appeared to be a result of a decrease in the cell population during liver formation. However, complete inhibition of liver development was not obtained. These results illustrate how LF2.8-EGFP transgenic zebrafish can be used as a simple and efficient tool for isolating and analyzing genes involved in liver development or function in zebrafish.

TABLE 3

Hepatogenesis in hhex and zXbp-1 morphants in 4 dpf LF2.8-EGFP zebrafish larvae

| Phenotype | Control morpholino 400 ng/µl | hhex morpholino 800 ng/µl | hhex morpholino 400 ng/µl | hhex morpholino 100 ng/µl |
|---|---|---|---|---|
| Normal liver | 96 (95%) | 2 (1%) | 5 (2.5%) | 34 (17%) |
| Reduced liver | 0 (0%) | 151 (75.5%) | 186 (93%) | 160 (80%) |
| Other defect | 2 (2%) | 22 (11%) | 3 (1.5%) | 2 (1%) |
| Dead | 3 (3%) | 25 (12.5%) | 6 (3%) | 4 (2%) |

| Phenotype | Control morpholino 400 ng/µl | zXbp-1 morpholino 1600 ng/µl | zXbp-1 morpholino 800 ng/µl | zXbp-1 morpholino 200 ng/µl |
|---|---|---|---|---|
| Normal liver | 97 (97%) | 3 (1.5%) | 8 (4%) | 61 (30.5%) |
| Reduced liver | 0 (0%) | 163 (81.5%) | 178 (89%) | 126 (63%) |
| Other defect | 1 (1%) | 19 (9.5%) | 5 (2.5%) | 4 (2%) |
| Dead | 2 (1%) | 15 (7.5%) | 9 (4.5%) | 9 (4.5%) |

Embryos were injected with approximately 2.0 nl of the morpholino (MO) solution per embryo. Control morpholinos for hhex and zXbp-1 were designed by four base mutations compared to their original MO sequence.

F. Summary of the Findings

The present invention demonstrated detailed analysis and characterization of expression control sequences that regulate expression of the zebrafish L-FABP gene. Expression of L-FABP had previously been reported in the liver of adult zebrafish. Stable transgenic zebrafish lines carrying such expression control sequences operably linked to a reporter gene have also been generated.

In virtually all seven zebrafish lines established, no positional effect of the integration sites was found. These seven independent transgenic lines show continual stable transmission and high level of GFP expression in liver and have been maintained for over six generations. The transgenic embryos from each line displayed an identical fluorescent liver pattern, and no variegated GFP expression was seen in any other regions of the embryos. This presents a strategy for using the L-FABP promoter to drive GFP in liver without affecting either early embryonic liver development or adult liver function. Thus, the results indicate that the zebrafish L-FABP promoter can reliably drive reporter gene expression in an identical manner as the endogenous L-FABP gene in transgenic zebrafish. This is the first demonstration of transgenic zebrafish in which a reporter gene is driven by a liver-specific promoter.

II. The 435 bp Liver Regulatory Sequence in the L-FABP Gene is Sufficient to Modulate the Liver Regional Expression in Transgenic Zebrafish

A. Materials and Methods

1. Fish Maintenance

See Example IA above.

2. Transgenic DNA Constructs

The construction of the pLF2.8-EGFP plasmid used in this study has been described in Example I above. For the construction of 5' truncation of the pLF2.8-EGFP expression constructs, pLF2.5-EGFP, pLF2.0-EGFP, pLF1.8-EGFP, pLF1.5-EGFP, pLF1.2-EGFP, pLF1.0-EGFP, pLF0.8-EGFP and pLF0.5-EGFP were generated from this construct by PCR amplification using the 3' end primer (5'-AAC ACT CAA CCC TAT CTC GG-3') (SEQ ID NO:18) and primers specific to different regions of the 5' end L-FABP promoter (FIG. 2). The specific primers for amplification of LF2.5-EGFP, LF2.0-EGFP, LF1.8-EGFP, LF1.5-EGFP, LF1.2-EGFP, LF1.0-EGFP, LF0.8-EGFP and LF0.5-EGFP were LF2.5 (5'-CGG ATG GGC TGC TCT GAG TA-3') (SEQ ID NO:19), LF2.0 (5'-AAG GTC AAT ATT ATT AGC CC-3') (SEQ ID NO:20), LF1.8 (5'-TGT GCT GAA ACA ATC TGC TC-3') (SEQ ID NO:21), LF1.5 (5'-CTC TGA ATA ATT TTT TCA GT -3') (SEQ ID NO:22), LF1.2 (5'-TTA TTA GAG ACT AAT CTT TG-3') (SEQ ID NO:23), LF1.0 (5'-GAA TCA ATC CTG CAG GTC AA-3') (SEQ ID NO:24), LF0.8 (5'-CAG ATC ATG TCT ATG CAT TT-3') (SEQ ID NO:25) and LF0.5 (5'-GTA TCA AAA TCT CTT TTG AT-3') (SEQ ID NO:26), respectively. All PCR products were cloned into the pGEM-T vector (Promega). To generate LF2.8-LR, pLF2.8-EGFP was double-digested with Xca I/Sty I (−1944 −1510) and the larger DNA fragment was isolated and self-ligated. For enhancer vectors, SV40+LR construct was made by inserting a Xca I/Sty I DNA fragment upstream of the basal early SV40 promoter region of SV40-EGFP reporter construct (Clontech). To make specific deletions or mutations of the consensus sites in the Xca I/Sty I DNA fragment, primers used for PCR deletion of the A and B regions and PDX1(1), PDX1(2), HFH(1), HFH(2), NHF-1α and HNF-3β sites were designed as complementary pairs of oligonucleotides to the distal region of 5' flanking sequence of L-FABP. Then the deleted Xca I/Sty I DNA fragments were cloned into the SV40-EGFP reporter construct; resultant constructs were name SV40-A, B, PDX1(1), PDX1(2), HFH(1), HFH(2), NHF-1α and HNF-3β, respectively. All recombinant vectors were sequenced to confirm the sequences of regions of interest.

3. Microinjection of Zebrafish Embryos and Generation of Transgenic Zebrafish Lines To construct a permanent transgenic line, SV40+LR and its derivatives described above were linearized by digesting the vector backbone with Sal I and Not I. Digested DNA was adjusted to 500 ng/µl in 5 mM Tris, 0.5 mM EDTA, 100 mM KCl and 0.1% phenol red. For transient expression, an intact circular form of the plasmid DNA constructs was adjusted to 100 ng/µl. Approximately 200 pl of the DNA solution was injected into the blastomere of the early one-cell stage embryos using a glass micropipette. At 36 h post-injection, the fish were examined using fluorescent microscopy and GFP expressing fish were saved. Germ-line integrated transgenic zebrafish were selected from these GFP positive fish by raising them to sexual maturity and breeding them with wild-type fish. Progeny from these fish (at least 100 progeny) were screened for GFP expression and GFP-positive fish were saved for further analysis and breeding. We maintained these lines for four generations.

4. Optics

For analyzing GFP fluorescent patterns, embryos and larvae were anesthetized with 168 mg/ml 3-aminobenzoic acid ethyl ester (Sigma). For the section of the green fluorescent liver, the GFP liver isolated from a scarified transgenic zebrafish adult was fixed overnight at 4° C. in PBS containing 4% paraformaldehyde, washed with PBS, cryoprotected in 30% sucrose, frozen in OCT (Miles Inc.) and sectioned at 15 mm on a cryostat. GFP expression was examined under a GFP filter (480 nm excitation, 505 nm emission) using an ECLIPSE E600 microscope (Nikon) equipped with the DXM 1200 CCD camera (Nikon).

B. Sequence Analysis of the L-FABP Upstream Region for Transcriptional Regulatory Regions Before embarking on additional functional mapping studies of the 5'flanking region of zebrafish L-FABP gene, we surveyed the sequence of its nucleotides −2783 to −1 (the nucleotide sequence has been deposited in GenBank under Accession No. AF512998). Using the Genomatix MatInspector database (www.genomatix.de), many putative transcription factor binding sites were found in the 2.8-kb L-FABP upstream region. In the proximal region (FIG. 7), several potential sites for developmental regulatory factors were found including six consensus motifs (at −384/−402, −489/−507, −527/−545, −701/−719, −743/−752, and −812/−830) for Cdx2, the intestine specific homeodomain protein (Silberg et al., 2000. *Gastroenterology* 119, 961-71). In addition, the nucleotide sequence for the immediate upstream region (position −51 to −333) of the translation start site revealed a TATA-like sequence (−51/−58) and two CAAT boxes (−265/−273 and −334/−333), suggesting that the core promoter for L-FABP is located around this region.

Figure 8:
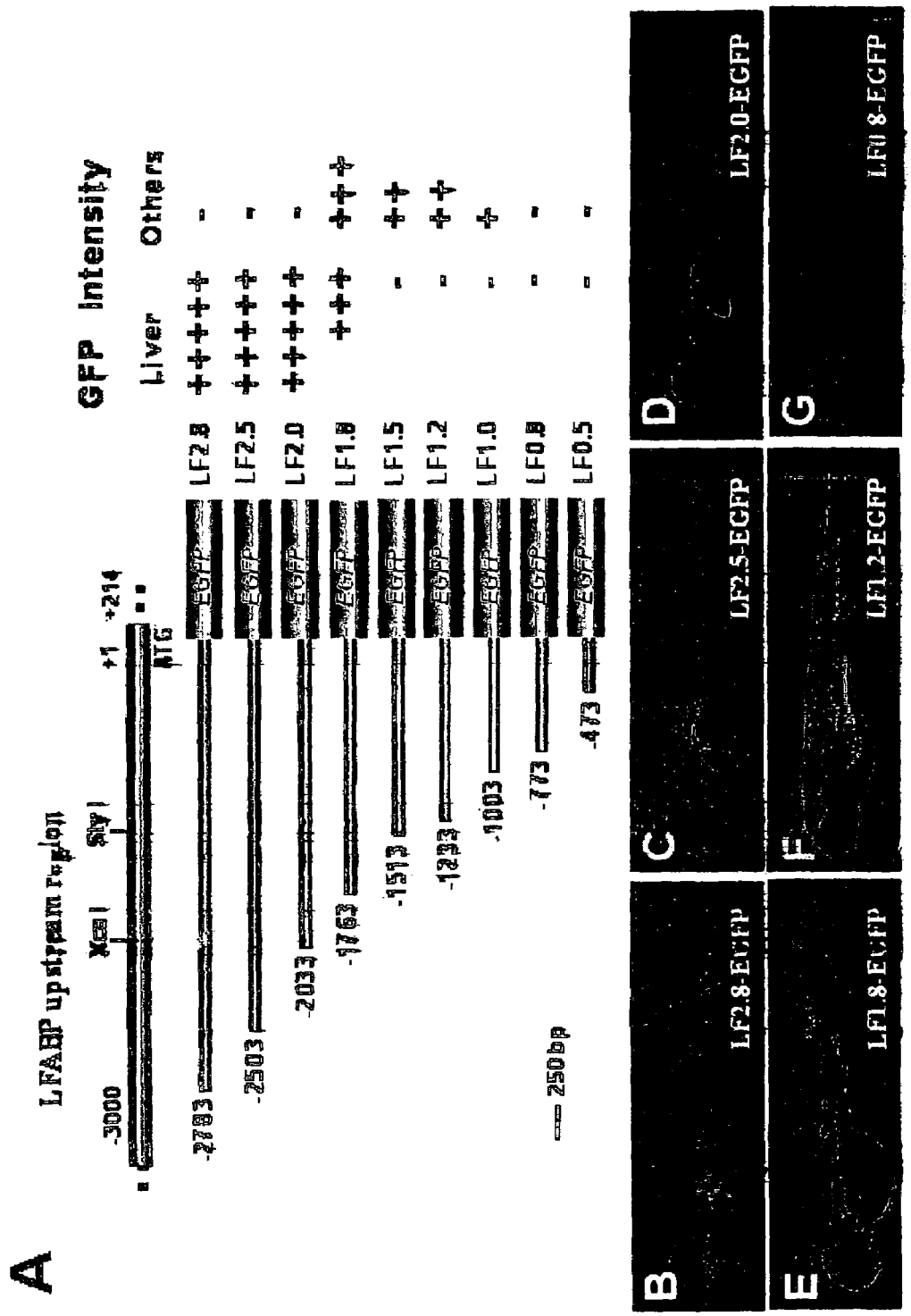
FIG. 8 shows constructs carrying deletions of the L-FABP upstream region which were used to identify sequences that allow efficient, liver-specific transcription in transient assays.

C. The 2.0 kb 5° Flanking Sequence Conferred Correct Liver Specific and Developmentally Regulated Expression of GFP in Transgenic Zebrafish To address the regulation of L-FABP expression in vivo and to examine how much of the 5'flanking sequence in the 2.8 kb L-FABP promoter region fragment is sufficient for spatio-temporal control of GFP expression, we have mapped cis-acting sequences responsible for L-FABP expression in zebrafish larvae. Deletions of the 5' flanking region of L-FABP fused to a GFP reporter gene (FIG. 8A, left) were analyzed. The LF2.8-EGFP and eight deletion constructs were individually injected into zebrafish embryos at the one-cell stage and then GFP expression in the microinjected embryos was analyzed using fluorescence microscopy (FIG. 8A right). As shown, when LF2.8-EGFP, LF2.5-EGFP and LF2.0-EGFP were microinjected, over 80% of the microinjected embryos had similar GFP expression in the developing liver primordia at 72 hours post fertilization (hpf) (FIGS. 8B-8D). Only 31% of embryos microinjected with LF1.8-EGFP displayed GFP expression in the developing liver of 72 hpf embryos but nearly 70% of embryos showed non-specific expression (FIG. 8E). No GFP-positive cells were seen in the developing liver primordia of the embryos microinjected with deletion constructs LF1.5-EGFP, LF1.2-EGFP (FIG. 8F) and LF1.0-EGFP but all showed non-specific expression. No GFP fluorescence was seen in the embryos microinjected with either LF0.8-EGFP (FIG. 8G) or LF0.5-EGFP.

Together, embryos injected with the deletion construct of LF1.8-EGFP had reduced liver specific GFP expression and significantly increased non-specific expression compared with GFP expression of the embryos injected with LF2.8-EGFP, LF2.5-EGFP or LF2.0-EGFP constructs. Embryos injected with the LF1.5-EGFP, LF1.2-EGFP or LF1.0-EGFP constructs showed no liver specific GFP expression or non-specific GFP expression. Embryos injected with the deletion constructs of LF0.8-EGFP or LF0.5-EGFP, showed no GFP expression at all. These results suggested that a 435 bp sequence region (−1944 to −1510) is important for liver-specific activity and that the 1.0 kb of 5' flanking sequence contains the core promoter for the zebrafish L-FABP gene. Thus, the 2.0 kb of 5' flanking sequence in the LF2.0-EGFP construct contains promoter regions and/or regulatory elements necessary to restrict L-FABP gene expression to the liver.

Figure 9:
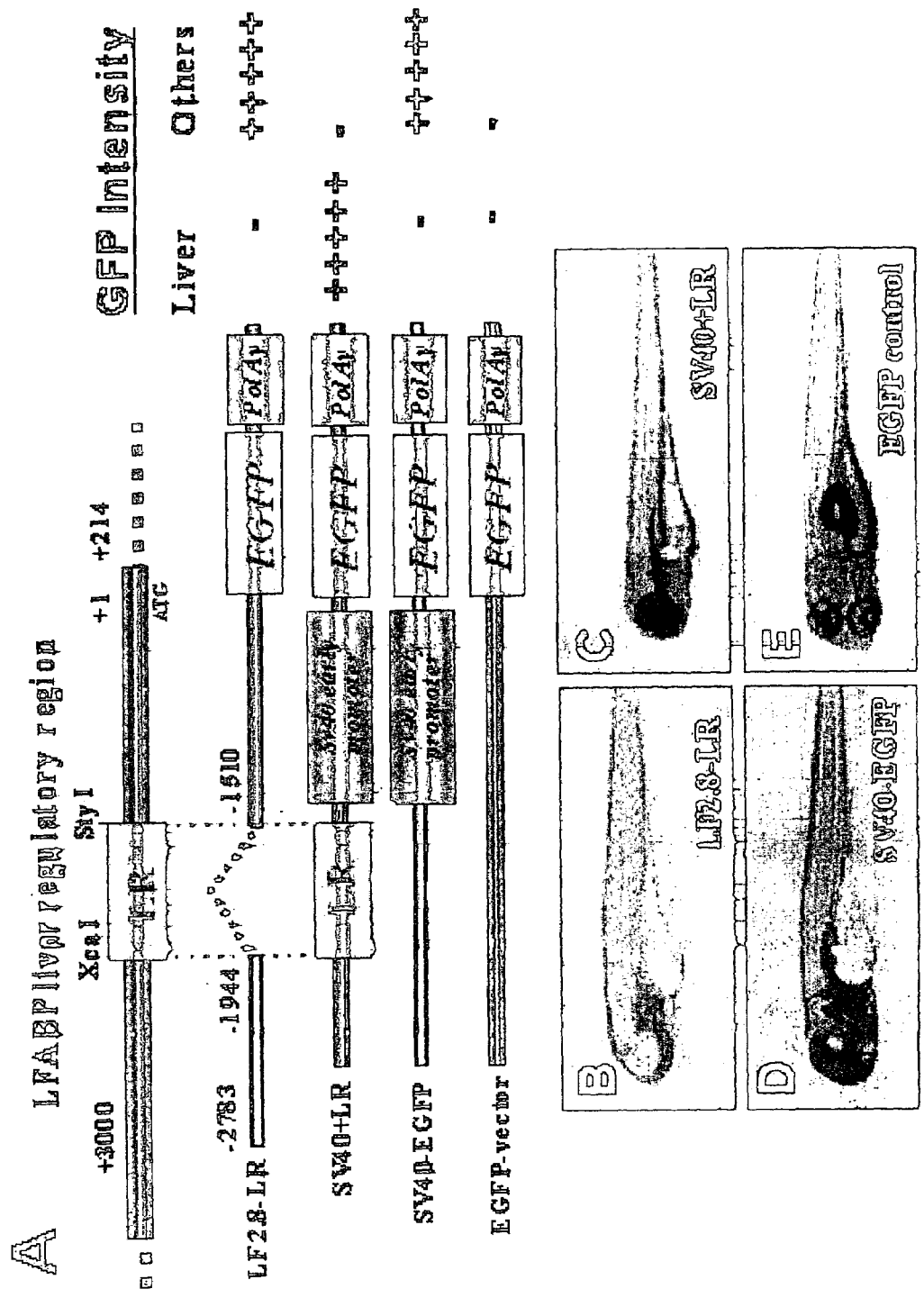
FIG. 9 shows the expression of GFP of the SV40+LR construct, and various controls.

D. Upstream 435 bp Sequence Recapitulated the Promoter Activity of L-FABP Gene in the Liver Throughout Embryonic Development and Adulthood Comparison of the transient expression with the LF-EGFP constructs suggested that a liver specific regulatory sequence (LR) may lie between −1944 and −1510 (FIG. 8A left). To test this hypothesis, an internal deletion mutant, LF2.8-LR, was created, in which the −1944 to −1510 region was deleted from within the LF2.8-EGFP construct (FIG. 9A left, LF2.8-LR). Embryos microinjected with LF2.8-LR retained GFP expression in the yolk and eyes but no GFP expression was seen in the liver (FIGS. 9A left, LF2.8-LR and 9B).

To further identify the 435 bp sequence as a liver specific regulatory element, the 435 bp sequence was inserted into the 5' end of the SV40-EGFP construct (Clontech) which contained a basal SV40 promoter and generated a new construct (SV40+LR). Embryos microinjected with SV40+LR displayed GFP expression in the liver (FIGS. 9A left, SV40+LR and 3C). For the negative control, embryos microinjected with the SV40 basal promoter linked to EGFP (SV40-EGFP) displayed GFP expression in yolk (FIGS. 9A left, SV40-EGFP and 9D). No GFP expression was seen in the embryos microinjected with the GFP reporter gene construct (FIGS. 9A left, EGFP-vector and 3E).

Figure 10:
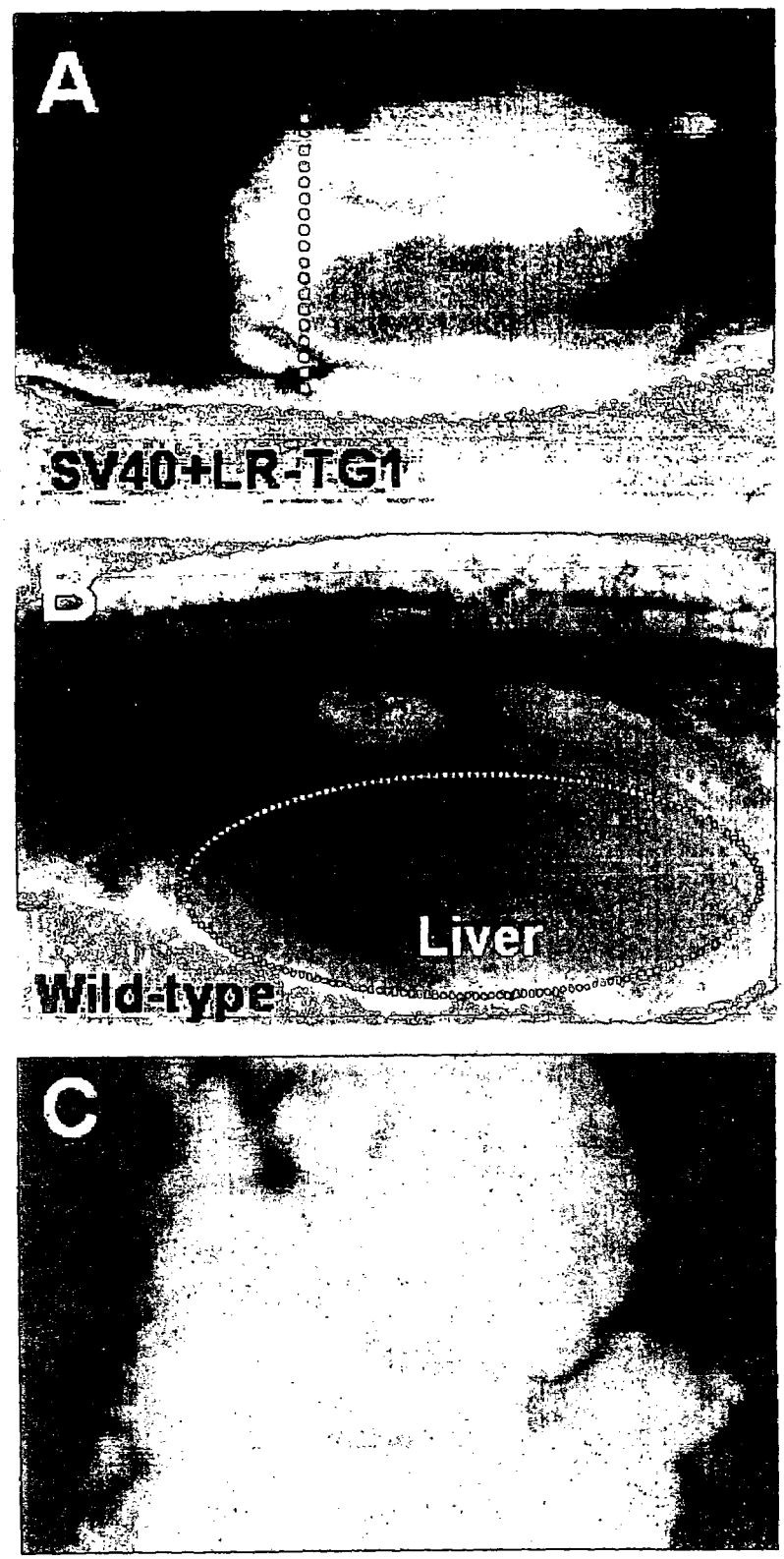
FIG. 10 shows expression of GFP in the liver at various times of development.

To examine the expression of GFP in the liver cells of adult transgenic fish, three SV40+LR transgenic lines were generated. At 6 months of development, GFP expression in the liver was still quite detectable (FIG. 10A) and there were no visible defects in the liver compared with the wild-type liver (FIG. 10B). A transverse cryosection of the liver from a 6-month-old transgenic fish was examined and individual GFP-labeled liver cells (hepatocyte) with substantial green fluorescence were clearly seen in the liver (FIG. 10C). Thus, the LR sequence within the distal region of 5' flanking region of zebrafish L-FABP gene was sufficient to activate liver specific gene expression during early embryonic stages of lineage determination and to maintain L-FABP expression in the cells of the adult liver.

Figure 12:
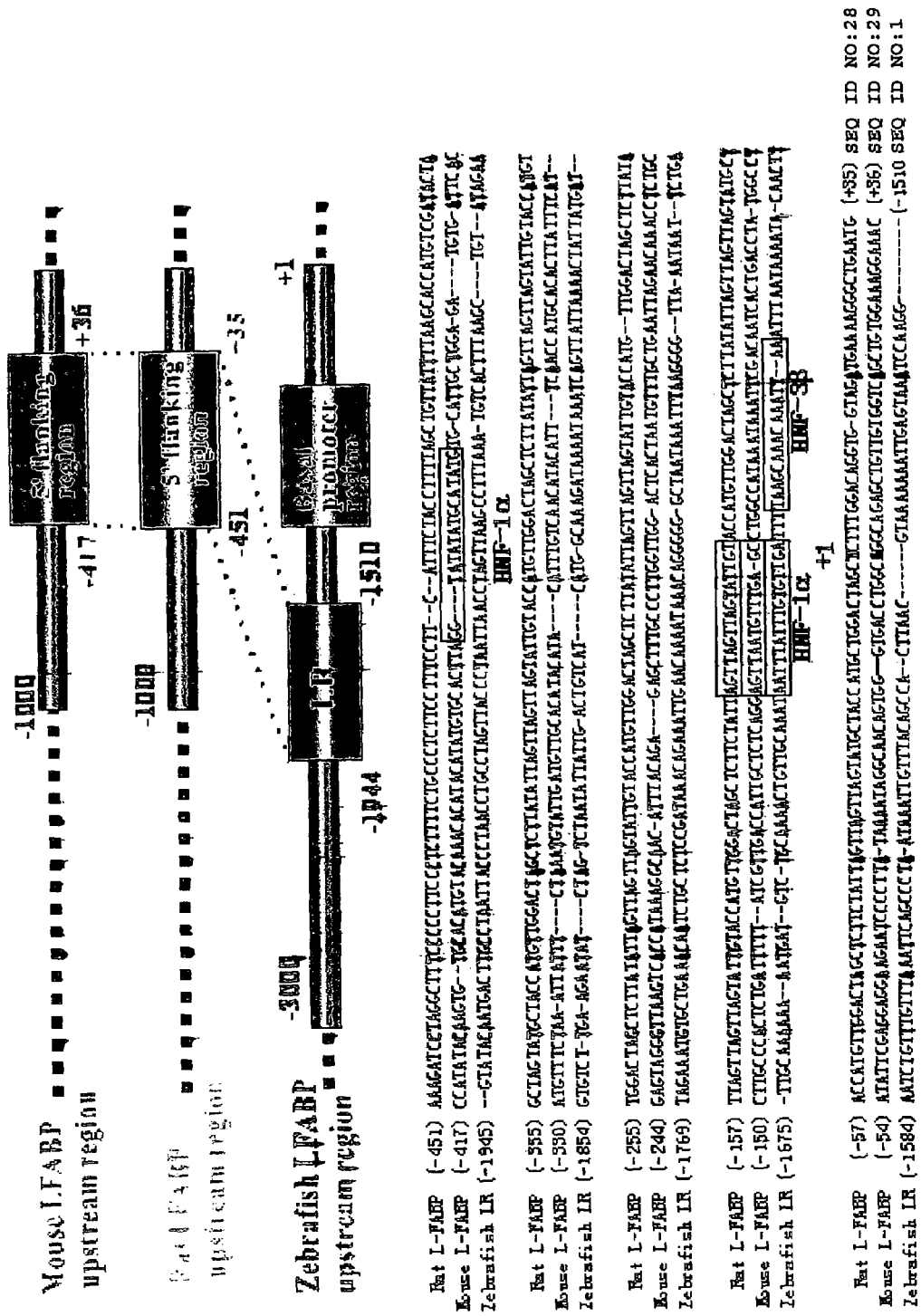
FIG. 12 compares the L-FABP upstream regions of mouse, rat and zebrafish.

E. Conservation of the HNF1-α Binding Site Among Orthologous Rat Mouse and Zebrafish L-FABP Genes Sequence analysis of the LR region revealed a cluster of putative transcription factor consensus binding sites present within −1983 to −1504 (FIG. 11 and FIG. 13A). Among these sites several are for known to have liver-enriched transcription factors including a consensus HNF-1α binding site (−1703 to −1699) (Tronche et al., 1992. *Bioessays* 14, 579-87), a consensus HNF-3β binding site (−1616 to −1612) (Overdier et al., 1994. *Mol Cell Biol* 14, 2755-66), and two motifs for hepatocyte nuclear factor 3/fork head homolog (HFH) (−1739 to −1734 and (−1719 to −1714) (Peterson et al., 1997. *Mech Dev* 69, 53-69). Other potentially important developmentally regulated sites include the motifs for the pancreatic and intestinal homeodomain protein Pdx1(IDX1/IPF1) (−1927 to −1922 and −1900 to −1985) (Ohlsson et al., 1993. *Embo J* 12, 4251-9). In the comparison of 5' flanking sequences of mouse (Akiyama et al., 2000. *J Biol Chem* 275, 27117-22), rat (accession number AF329653), and zebrafish L-FABP, a small number of identical sequences were seen among the 5' flanking region of zebrafish, mouse and rat L-FABP genes. Interestingly, a common HNF1-α consensus binding site exists among the rat L-FABP promoter at −343 to −328 bp, the mouse L-FABP promoter at −368 to −353 bp and the LR region of zebrafish L-FABP promoter at −1638 to −1623 bp relative to the transcriptional start site (FIG. 12).

In recent studies, L-FABP was directly activated through cognate sites by HNF-1α and HNF-1β, as well as five other endodermal factors. In fact, L-FABP gene expression was found to be sharply diminished in the livers of the HNF-1α$^{-/-}$ mice compared with the heterozygous control subjects (Akiyama et al., 2000, supra). The presence of those potential consensus binding sites in the LR region of zebrafish L-FABP prompted us to examine their functional roles in the transcriptional regulation of the zebrafish L-FABP gene during embryogenesis.

F. Putative NHF-1α, HNF-3β and HFH Binding Sites in the LR Regulatory Sequence are Required for Efficient, Specific L-FABP Gene Expression In Vivo In order to further define the transcriptional regulatory domains in the 435 bp sequence responsible for the L-FABP gene expression in initial steps of hepatic specification, deletion analyses of the putative binding motifs in the 435 bp sequence were performed. The 435 bp liver regulatory region (−1944 to −1510) containing two distinct liver specific A (−1944 to −1623) and B (−1622 to −1510) elements were inspected (FIG. 13A). These two elements included binding sites of transcription factors that were involved in the liver specific gene expression and were able to specifically activate GFP expression in the liver (FIG. 13B right), respectively. To begin to assess the significance of these sites, a further deletion that removed one of those binding sites in the SV40+LR construct was created (FIG. 13B left). Eight mutation constructs were individually injected into zebrafish embryos during the one-cell stage and then GFP expression in the microinjected embryos was analyzed using fluorescence microscopy. As shown, deletion of the two PDX sites in the A element had no significant effects on the liver activity (FIG. 13C,D). However, deletion of either of the two HFH sites or the HNF-1α site in the A element or the A element (FIGS. 13E,F,G,I) or HNF-3β site in the B element or the B element (FIGS. 13H and J) significantly altered specificity in the liver primordia of 96 hpf larvae.

Taken together, the putative NHF-1α, HNF-3β and HFH binding sites in the LR sequence are truly required for efficient, specific L-FABP gene expression in vivo. In addition, the HNF-1α consensus site most likely to has the function of the L-FABP gene regulation in vertebrates.

G. Summary of the Findings

The chimeric construct (SV40+LR) has a similar expression pattern compared with the LF2.8-EGFP construct while SV40+LR has a weaker liver specific promoter activity than that of the LF2.8-EGFP during zebrafish larval development. The results suggested that other regulatory sequences may exist within the 2.8 kb promoter region.

The results of our functional analysis of several hepatocyte nuclear factor binding sites in the zebrafish reporter constructs are consistent with studies in other vertebrates, such as, e.g., rats and mice. Compare, e.g., Simon et al. (1993). *J Biol Chem* 268, 18345-358. The importance of the two HFH and one HNF-1α binding sites in the A element and the one HNF-3β binding site in the B element within the 435 bp distal region of the zebrafish L-FABP promoter region suggests that a combination of interactions between multiple regulatory factors are responsible for the gene expression of L-FABP in the liver.

In addition the HNF-1α, HNF-3β and HFH binding sequences, two Pdx-1 and six Cdx-2 binding motifs were also found in the LR and proximal region of the 5' flanking region of the zebrafish L-FABP gene, respectively. Neither of the two Pdx binding motifs nor the seven Cdx2 binding motifs was essential for tissue specific expression in the embryos microinjected with the LF0.8-EGFP or the LF0.5-EGFP construct, respectively. However, we cannot completely rule out the possibility that other genes involved in the development of the pancreas or intestines might also regulate the L-FABP expression during hepatogenesis.

Three GFP-expressing transgenic lines using the SV40+ LR constructs were generated. In virtually all three lines that were established, no positional effects of the integration sites were found because transgenic embryos from each line displayed a nearly identical fluorescent liver pattern. In addition, no variegated GFP expression was seen in any other regions of the embryos. These results suggest that the LR sequence act both independently and in concert to generate the liver specific expression in the embryonic and adult liver of the zebrafish.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

We claim:

1. An isolated polynucleotide comprising a chimeric construct comprising a liver-specific expression control sequence that modulates expression of a vertebrate liver fatty acid binding protein (L-FABP) and wherein said liver-specific expression control sequence comprises the nucleic acid sequence of SEQ ID NO:1.

2. The isolated polynucleotide according to claim 1, wherein said nucleic acid sequence is isolated from zebrafish.

3. The isolated polynucleotide according to claim 1, wherein said liver-specific expression control sequence comprises the nucleic acid sequence of SEQ ID NO:2.

4. The isolated polynucleotide according to claim 1, wherein said liver-specific expression control sequence comprises the nucleic acid sequence of SEQ ID NO:3.

5. The isolated polynucleotide of claim 3, wherein said nucleic acid sequence is isolated from an upstream region of a gene encoding a zebrafish L-FABP.

* * * * *